(12) United States Patent
Sarill et al.

(10) Patent No.: US 6,274,564 B1
(45) Date of Patent: Aug. 14, 2001

(54) COMPOSITIONS OF COBALAMIN AND RELATED CORRINOIDS, AND USES THEREOF

(76) Inventors: William J. Sarill, 78 Hibbert St., Arlington, MA (US) 02154; Thomas F. Brennan, 44 A Gail Dr., Nyack, NY (US) 10960

( * ) Notice: Subject to any disclaimer, the term of this patent is extended or adjusted under 35 U.S.C. 154(b) by 0 days.

(21) Appl. No.: 08/936,781

(22) Filed: Sep. 17, 1997

Related U.S. Application Data

(60) Provisional application No. 60/041,750, filed on Mar. 28, 1997, and provisional application No. 60/025,298, filed on Sep. 18, 1996.

(51) Int. Cl.⁷ .................. A61K 31/70; A61K 31/195
(52) U.S. Cl. .................... 514/52; 514/561; 514/563; 514/567
(58) Field of Search ................ 514/52, 561, 563, 514/567

(56) References Cited

U.S. PATENT DOCUMENTS

| | | | |
|---|---|---|---|
| 5,039,668 | 8/1991 | Colina | 514/52 |
| 5,716,941 | 2/1998 | Rabinoff | 514/52 |

FOREIGN PATENT DOCUMENTS

| | | |
|---|---|---|
| 1345327 | 1/1994 | (EP) . |
| 48021484 | 7/1965 | (JP) . |
| WO 98/19690 | 5/1998 | (WO) . |

OTHER PUBLICATIONS

Matera, et al. "Pharmacokinetic Study of the Relative Bio-availability and Bioequivalence After Oral Intensive or Repeated Short Term Treatment with Two Polyamino Acid Formulations" *Int. J. Clin. Pharm. Res.* XIII(2) 93–105 (1993).

Dekoninck et al 94 CA 154479R, 1981.*
Basun et al 115 CA 156375e, 1991.*
Nadeau et al 110 CA 153177c, 1989.*

* cited by examiner

*Primary Examiner*—Russell Travers
(74) *Attorney, Agent, or Firm*—Lahive & Cockfield, LLP

(57) ABSTRACT

Novel compositions cobalamin and related corrinoids, and uses thereof, are disclosed. The novel compositions include a corrin, a first amino acid having a side chain which includes a basic or positively charged moiety; and a second amino acid with an uncharged side chain which includes at least one heteroatom. The compositions are useful for, inter alia, treatment of cobalamin deficiency.

17 Claims, No Drawings

COMPOSITIONS OF COBALAMIN AND RELATED CORRINOIDS, AND USES THEREOF

CROSS-REFERENCE TO RELATED APPLICATIONS

This applications claims benefit under 35 U.S.C. 119(e) to co-pending U.S. provisional applications Ser. No. 60/025,298, filed Sep. 18, 1996, and Ser. No. 60/041,750, filed Mar. 28, 1997; the contents of which are hereby incorporated by reference.

BACKGROUND OF THE INVNETION

The cobalamin family comprises vitamin B12 (cyanocobalamin) and its axial-ligand substituted congeners, such as hydroxocobalamin, methylcobalamin and adenosylcobalamin, among others. Various cobalamins have been used effectively for the treatment of conditions resulting from cobalamin deficiency, such as hematological abnormalities (e.g., macrocytosis and megaloblastic anemia) and neurological impairments (ranging from neuropathy and demyelination to confusional states, mood shifts, memory loss, dementia and depression). These classical sequelae to chronic vitamin B12 deficiency and their treatment are well known (Schneider and Stroinski, *Comprehensive B12* (New York: Walter de Gruyter & Co., 1987)). In addition, a number of other diseases or disease states have been characterized by some form of cobalamin deficiency; in many of these cases cobalamin treatment has been reported to result in an amelioration of symptoms or other improvement in the patient's condition. The diseases and disease states studied include anemias of various kinds, autoimmune conditions, disorders of carbohydrate and lipid metabolism such as diabetes and atherosclerosis, neuropathies of various etiologies, mitochondrial disorders and/or deficiencies of cellular bioenergetics, neurodegenerative diseases, mental and psychiatric disorders, endocrine dysfunctions, infertility and reproductive disorders, osteoporosis, immunodeficiencies, AIDS and cancer.

Erythrocyte macrocytosis and macrocytic anemia are often considered to be the classic hematological signs of cobalamin deficiency, especially when found in conjunction with low hemoglobin values. Recently, however, a more complex and varied picture of cobalamin-deficiency anemia has emerged. For example, a surprisingly high rate of incidence of cobalamin deficiency has been detected in sickle cell disease (SCD) patients (Carmel & Johnson, Blood 86, Suppl. 1,644a (1995); Al-Momen, J. Intern. Med. 237, 551–555 (1995)), where the sickle cell anemia may mask a coexisting cobalamin deficiency anemia. The frequent association of folate deficiency with SCD further obscures and complicates the clinical picture. In particular, investigators have concluded that the frequency of cobalamin abnormalities is high enough to warrant concern about the indiscriminate use of folate supplements in SCD (Carmel & Johnson, op. cit.), since folate administration in the absence of cobalamin is known to exacerbate the neuropathology of cobalamin deficiency. Thus, cobalamin supplementation may be especially desirable in those SCD patients who are being treated with folate. Furthermore, an increased unsaturated B12 binding capacity has been unexpectedly found in association with iron deficiency anemia (Rosner & Schreiber, Am. J. Med. Sci. 263, 473–480 (1972)) suggesting an increased need for vitamin B12 under these circumstances. Delayed plasma clearance of radiolabeled cobalamin has also been reported in iron deficiency anemia; one explanation proposed for this effect is a decreased uptake of vitamin B12 by tissues as a result of diminished erythropoiesis (Cook & Valberg, Blood 25, 335–344 (1965)). Since ethrythrocytes appear to play a significant role in delivering cobalamin to tissues (Sorrell et al., Am. J. Clin. Nutr. 24 924–929 (1971)), one may conclude that any cause of anemia resulting in diminished erythropoeisis and/or decreased red cell numbers can induce a state of functional cobalamin deficiency. Therefore, cobalamin supplementation may be useful in treating various forms of anemia and especially in treating those cases associated with coexisting folate deficiency, e.g., as in thalassemia (Kumar et al., Am. J. Clin. Pathol. 84,668–671 (1985)) or SCD.

Pernicious anemia, the prototypical disorder of cobalamin absorption, is generally characterized by gastric atrophy and autoimmune attack on the parietal cells of the gastric fundus, with consequent depletion or impairment of intrinsic factor. Suggestively, an increased prevalence of other autoimmune disorders, such as vitiligo, Graves' disease, Hashimoto's thyroiditis, Type I diabetes, Sjogren's syndrome and rheumatoid arthritis, is found among pernicious anemia patients; the resulting pattern of coexisting autoimmune disease is referred to by the term polyglandular autoimmune syndrome (Leshin, Am. J. Med. Sci. 290, 77–88 (1985)). Many autoimmune disorders, whether components of a polyglandular autoimmune syndrome or not, are associated with abnormal cobalamin metabolism. For example, cases of Sjogren's syndrome, rheumatoid arthritis, systemic lupus erythematosus, dermatomyositis and autoimmune hemolytic anemia have been associated with elevated levels of apo-transcobalamin II, the unbound form of the B12-binding protein which carries cobalamin from serum to cells, thus suggesting an increased demand for vitamin B12 in these conditions (Gimsing et al., Scand. J. Rheumatol. 11, 1–4 (1982); Frater-Schroder et al., Lancet 2, 238–239 (1978)). Furthermore, cobalamin deficiencies have been noted in both synovial fluid (Ono et al., J. Vitaminol. 18, 1–2 (1972)) and serum (Vreugdenhil et al., Ann. Rheum. Dis. 49, 93–98 (1990)) of patients with rheumatoid arthritis, and in the sera of patients with systemic lupus erythematosus (Molad et al., Am. J. Med. 88, 141–144 (1990)), inclusion body myositis and Sjogren's syndrome (Khraishi et al., J. Rheumatol. 19, 306–309 (1992)). A number of these conditions have been shown to be responsive to cobalamin therapy. For example, methylcobalamin has been reported efficacious in the treatment of rheumatoid arthritis (Yamashiki et al., J. Clin. Lab. Immunol. 37, 173–182 (1992)). Likewise, some cases of multiple sclerosis are associated with cobalamin deficiency (Reynolds et al., Arch. Neurol. 48, 808–811 (1991); Baig & Qureshi, Biogenic Amines 11, 479–485 (1995)), and improvement in some patients has been noted upon treatment with cyanocobalamin (Levin, Am. J. Digest. Dis. 22, 96–97 (1955)) or methylcobalamin (Kira et al., Intern. Med. 33, 82–86 (1994)). Both psoriasis and lupus erythematosus have been successfully treated with cyanocobalamin (Stingily, Miss. Doctor 32, 222–223 (1955)), while cases of vitiligo have responded to treatment with vitamin B12 combined with other vitamins (Montes et al., Cutis 50, 39–42 (1992)).

Several distinct lines of evidence connect cobalamin deficiency with diabetes mellitus and other disorders of carbohydrate metabolism. In animals rendered experimentally diabetic, a significant decrease in both serum and tissue cobalamins has been shown to accompany the induction of ketosis (Nath & Nath, J. Vitaminol. 15, 174–177 (1969)). Elevated levels of unsaturated B12 binding capacity (UBBC), a measure of apo-transcobalamins in serum, have been noted in diabetic patients with hyperglycemia, with UBBC normalizing upon restitution of glycemic control (Takahashi et al., Diabetes Res. Clin. Pract. 25, 13–17 (1994)). Moreover, it has long been known that insulin resistance is common among patients presenting with both diabetes and pernicious anemia (Adams, Med. Clin. N. Amer. 8, 1163–1170 (1925); Wright, Clifton Med. Bull. 12, 64–67 (1926)), whereas vitamin B12 administration is effective in increasing insulin sensitivity in some diabetics (Ralli et al., J. Clin. Endocrinol. Metab. 15, 898 (1955)). Likewise, treatment of pernicious anemia patients with cyanocobalamin is known to improve glucose tolerance, an effect attributed to the regulatory influence of vitamin B12 on carbohydrate metabolism (Panzram, Schweiz. Med. Wschr. 91, 234–240 (1961)). Vitamin B12 has also been reported effective in restoring the impaired glucose tolerance induced by thyroid hormone, corticosteroids and by various disease processes (Hadnagy et al., Int. Z. Vitaminforsch. 33, 141–150 (1963)). Since Type II diabetes, obesity, hypertension, coronary artery disease and age-related glucose intolerance have all been associated with increased insulin resistance (Reaven, Diabetes 37, 1595–1607 (1988); Jackson, Diabetes Care 13, Suppl. 2, 9–19 (1990)), cobalamin supplementation is likely to be of specific benefit in these conditions. Alcoholism is another disease associated with impaired glucose tolerance (Dobbins, U.S. Pat. No. 4,918,102 (4/17/90)). Tissue levels of vitamin B12 have been reported depleted in chronic alcoholism (Kanazawa & Herbert, Lab. Invest. 53, 108–110 (1985)), thus offering a rationale for supplementation. In addition, patients with cystic fibrosis (CF) often develop impaired glucose tolerance and progress to frank diabetes characterized by peripheral and hepatic insulin resistance (Hardin et al., Diabetes 44, Suppl. 1, 200A (1995)). CF also is known to be associated with aberrations in vitamin B12 absorption and transport (Lindemans et al., Acta Paediatr. Scand. 74, 795–796 (1985)).

Atherosclerosis involving renal, peripheral and cardiovascular sites is a major complication of diabetes mellitus; hyperinsulinemia and especially hyperglycemia are believed to contribute to the development of atherosclerosis by altering vascular metabolism and by inducing elevated lipid levels (Kunjathoor et al., J. Clin. Invest. 97 1767–1773 (1996)). As noted above, cobalamin supplementation can help normalize insulin sensitivity in diabetic patients and by implication reduce the risk of atherosclerotic involvement. Moreover, vitamin B12 deficiency has been shown to induce hypercholesterolemia in various animals (Hsu & Chow, Fed. Proc. 16, 63 (1957)), whereas treatment with vitamin B12 has been shown to attenuate the increase in serum cholesterol in an animal model of cholesterol-induced atherosclerosis (Nath & Saikia, Arch. Biochem. Biophys. 79, 216–233 (1959)). Obesity is another consequence of impaired glucose tolerance and a frequent concomitant of atherosclerosis. Animals maintained on a cobalamin-deficient diet with normal fat content tend to accumulate fat and become obese, while controls receiving vitamin B12 supplements remain normal (Ling & Chow, in Vitamin B12 und Intrinsic Factor (Stuttgart: Ferdinand Enke Verlag, 1957), 127–132).

Another factor predisposing to atherosclerosis is the accumulation of homocysteine in serum (Malinow, J. Intern. Med. 236, 603–617 (1994)). Cobalamin deficiency results in the failure of the cobalamin-dependent enzyme methionine synthase to remethylate homocysteine to methionine, with a consequent accumulation of homocysteine. Thus, deranged cobalamin metabolism can induce atherosclerotic lesions via elevated serum homocysteine (McCully, Nutr. Rev. 50 7–12 (1992)). Conversely, significant reductions in plasma homocysteine, cholesterol, triglycerides and low density lipoprotein have been observed in patients with ischemic heart disease treated with cyanocobalamin and other nutrients (Olszewski et al., Atherosclerosis 75 1–6 (1989); Olszewski, ibid. 88, 97–98 (1991)). Similarly, elevated plasma homocysteine in diabetic patients has been shown to be associated with clinical macroangiopathy, with reductions in homocysteine levels following upon treatment with methylcobalamin (Araki et al., Atherosclerosis 103, 149–157 (1993)). Cobalamin may be useful in the treatment of other homocysteine-related vascular occlusive disease, such as diabetic retinopathy (Neugebauer et al., Lancet 349, 473–474 (1997)) and arterial and venous thrombosis (Harpel et al., J. Nutr. 126, 1285S–1289S (1996)).

Diabetic neuropathy has been linked with a form of cobalamin deficiency in peripheral nerve (Tanaka et al., in *Diabetic Neuropathy* (Amsterdam: Excerpta Medica, 1982), 114–119). Effective treatment of diabetic neuropathy has been reported with cyanocobalamin (Sancetta et al., Ann. Intern. Med. 35, 1028–1048 (1951)), methylcobalamin (Yaqub et al., Clin. Neurol. Neurosurg. 94, 105–111 (1992)), and with hydroxocobalamin in combination with other B vitamins (Sakitama et al., J. Nutr. Sci. Vitaminol. 35, 95–99 (1989)). Methylcobalamin has also been found useful in the treatment of autonomic and peripheral neuropathies in uremic patients undergoing hemodialysis (Taniguchi et al., Clin. Ther. 9, 607–614 (1987)). Moreover, treatment with methylcobalamin has been shown to attenuate markedly the incidence of experimental allergic neuritis, an animal model of Guillain-Barre syndrome and other postinfectious and postvaccinal neuropathies (Inada et al., in *Vitamin B12* (Berlin: Walter de Gruyter & Co., 1979), 1017–1018). Other peripheral neuropathies which may be associated with cobalamin deficiency and for which cobalamin supplementation has been suggested include leprous neuropathy and the deficiency neuropathy of pellagra (Bedi et al., J. Assoc. Physicians India 21, 473–479 (1973)). In addition, some cases of orthostatic hypotension are known to be due to autonomic neuropathy secondary to cobalamin deficiency (Lossos & Argov, J. Am. Geriatr. Soc. 39, 601–602 (1991)). Likewise, instances of tinnitus (Shemesh et al., Am. J. Otolaryngol. 14, 94–99 (1993)) and optic neuritis (Heaton, Proc. Nutr. Soc. 19, 100–105 (1960)) may represent cases of sensory neuropathy treatable with cobalamin. Remarkably, even neuropathies of a genetic etiology may be treatable with cobalamin. For example, Leber's hereditary optic neuropathy (LHON) is a genetic disease associated with disturbances in cobalamin metabolism (Linnell et al., Clin. Sci. 37, 878 (1969)) and also with defects in mitochondrial DNA and electron transport activity (Rizzo, Neurology 45, 11–16 (1995)). The latter author has proposed that mitochondrial ATP depletion secondary to vitamin B12 deficiency is a metabolic trigger which can precipitate the symptomatology of LHON, and that supplementation with cobalamin (e.g., hydroxocobalamin) can enhance the potential for recovery.

It has long been recognized that cobalamin plays an important role in maintaining mitochondrial integrity (Reddi & Nath, J. Vitaminol. 17, 101–104 (1971)). One explanation for this effect involves the function of the mitochondrial enzyme methylmalonyl-CoA mutase, which utilizes adenosylcobalamin as coenzyme to catalyze the isomeization of L-methylmalonyl-CoA to succinyl-CoA. In cobalamin deficiency the activity of the enzyme is decreased and methylmalonic acid accumulates in plasma and tissues as a result (Toyoshima et al., J. Nutr. 125, 2846–2850 (1995)). Methylmalonic acid is a reversible inhibitor of succinate dehydrogenase, an enzyme which occupies a key locus at the intersection of the tricarboxylic acid cycle and the electron transport chain (Toyoshima et al., op. cit.; Dutra et al., J. Inher. Metab. Dis. 16, 147–153 (1993)). Defects in other components of the electron transport chain have also been noted in cobalamin deficiency (Krahenbuhl et al., J. Biol. Chem. 266, 20998–21003 (1991)), and it has been concluded that cobalamin deficiency can impair ATP synthesis by disrupting cellular bioenergetics (Nakai et al., Pediatr. Res. 30, 5–10 (1991)). This conclusion is significant not only for the understanding it provides of the pathogenesis of LHON (Rizzo, op. cit.), but also because decreased ATP levels and declining mitochondrial membrane potential have been proposed to initiate induction of apoptosis, or programmed cell death (Richter et al., FEBS Lett. 378, 107–110 (1996)). Apoptosis is thought to be involved in the pathogenesis of a number of conditions, including age-related diseases (Wolvetang et al., FEBS Lett. 339, 40–44 (1994)) and retroviral infections such those due to feline immunodeficiency virus (Danave et al., J. Virol. 68, 6745–6750 (1994)) and human immunodeficiency virus (HIV) (Macho et al., Blood 86, 2481–2487 (1995)). Inhibition of succinate dehydrogenase also results in secondary excitotoxicity which may play a role in hypoxia/ischemia and in neurodegenerative disease in general (Davolio & Greenamyre, Neurosci. Lett. 192, 29–32 (1995); Beal, Ann. Neurol. 38, 357–366 (1995)). All of these conditions may be initiated or promoted by cobalamin deficiency and, conversely, ameliorated by cobalamin therapy. Fibromyalgia (Bengtsson et al., Arth. Rheum. 20, 817–821 (1986)), Reye's syndrome (Partin et al., N. Engl. J. Med. 285, 1339–1343 (1971)) and other diseases associated with metabolic, viral, hypoxic or genetic disruption of cellular bioenergetics (Scholte, J. Bioenerg. Biomembr. 20, 161–191 (1988)) may likewise be amenable to treatment with cobalamin.

The neurotropic properties of cobalamins have led investigators to search for cobalamin deficiencies among cases of neurodegenerative disease. Alzheimer's disease has been characterized by low cobalamin levels in serum (Karnaze & Carmel, Arch. Intern. Med. 147, 429–431 (1987)), in cerebrospinal fluid (CSF) (Regland et al., Acta Neurol. Scand. 85, 276–281 (1992)), or in both (Ikeda et al., Acta Psychiatr. Scand. 82, 327–329 (1990)). Treatment with vitamin B12 has resulted in reduction of elevated platelet monoamine oxidase activity (Regland et al., Eur. Arch. Psychiatry Clin. Neurosci. 240, 288–291 (1991)) in Alzheimer's patients. In addition, patients exhibiting high CSF cobalamin levels after treatment with methylcobalamin have shown improvements in intellectual function and memory (Ikeda et al., Clin. Ther. 14, 426–437 (1992)) and in mood and sociability (Mitsuyama, in *Basic, Clinical, and Therapeutic Aspects of Alzheimer's and Parkinson's Diseases*, Vol. 2 (New York: Plenum Press, 1990), 15–18). Down's syndrome, a condition which eventually manifests a neuropathology resembling Alzheimer's disease in most patients over 40 (Ellis et al., Neurology 24, 101–106 (1974)), is also associated with macrocytosis and low serum B12 (Howell et al., Scand. J. Haemat. 11, 140–147 (1973)). Increases in IQ among children with Down's syndrome have been reported upon supplementation with high daily doses of cobalamin combined with other vitamins (Harrell et al., Proc. Natl. Acad. Sci. USA 78, 574–578 (1981)).

Other neuropathological conditions which may be associated with low serum cobalamin include amyotrophic lateral sclerosis and Parkinson's disease (Bauer & Heinrich, in *Vitamin B12 und Intrinsic Factor* (Stuttgart: Ferdinand Enke Verlag, 1957), 499–509). Improvement in some cases of amyotrophic lateral sclerosis has been reported upon treatment with vitamin B12 (Levin, Am. J. Digest. Dis. 22, 96–97 (1955); Krolyunitskaya et al., Zhur. Nevropat. Psikhiat. 56, 319–322 (1956)). Cobalamin deficiency has also been linked with excessive production of excitotoxic substances which may play a role in Huntington's disease (Brennan et al., Med. Hypotheses 7, 919–929 (1981)) and other neuropathologies (Santosh-Kumar et al., Med. Hypotheses 43, 239–244 (1994)). Conversely, recent studies have demonstrated a neuroprotective effect of methylcobalamin against the glutamatergic excitotoxicity induced by hypoxia/ischemia or by glutamate itself (Akaike et al., Eur. J. Pharmacol. 241, 1–6 (1993); Yarnamoto et al., Eur. J. Pharmacol. 281, 335–340 (1995)). Glutamatergic excitotoxicity of a related sort has been implicated in the pathogenesis of amyotrophic lateral sclerosis and Alzheimer's, Parkinson's and Huntington's diseases (Lipton & Rosenberg, N. Engl. J. Med. 330, 613–622 (1994)).

Neuropsychiatric disorders are common in cobalamin deficiency and often appear with minimal evidence of hematological abnormality; many of these conditions improve upon cobalamin administration (Lindenbaum et al., N. Engl. J. Med. 318, 1720–1728 (1988)). Some cases of schizophrenia have responded to treatment with vitamin B12 (Regland et al., J. Neural Transm. 98, 143–152 (1994)) or with B12 in combination with other B vitamins (Joshi et al., J. Orthomol. Psychiatry 9, 35–40 (1980)), even in the absence of overt cobalamin deficiency. An association among violent behavior, learning disabilities and low levels of cobalamin in hair samples has been described (Schrauzer et al., Biol. Tr. Element Res. 34, 161–176 (1992)). Since learning disabilities and aggression are frequent concomitants of attention deficit disorder (ADD) (Hallowell & Ratey, *Driven to Distraction* (New York: Pantheon Books, 1994)), the latter findings suggest a pathogenic role for cobalamin deficiency in ADD, a conclusion supported by reports that vitamin B12 administration is of benefit in treating distractibility and inattention in students (Robin, Semaine hop. Paris 30, 4129–4132 (1954)). Also low serum cobalamin levels have been found among cases of obsessive compulsive disorder (OCD) at a much higher frequency than among controls (Hermesh et al., Acta Psych. Scand. 78, 8–10 (1988)). OCD is believed to result from dysfunction of central serotonergic mechanisms, and abnormal serotonin metabolism has been found in cobalamin deficiency (Botez et al., Ann. Neurol. 12, 479–484 (1982)). Derangements involving serotonin and other neurotransmitters, such as norepinephrine (Deana et al., Int. J. Vit. Nutr. Res. 47, 119–122 (1977)) and GABA (Brennan et al., Brain Res. 219, 186–189 (1981)), may account for many of the mental, psychological and psychiatric disturbances known to accompany cobalamin deficiency. In addition, changes in thyroid function have been reported to be associated with onset of or recovery from depression (Levitt & Joffe, Biol. Psychiatry 33, 52–53 (1993)). Cobalamin deficiency is also known to be linked with depression; recently, the severity of depression in an outpatient population has been positively correlated with serum thyroxine and negatively correlated with serum cobalamin, suggesting an inverse relationship between thyroid hormone and vitamin B12 in the regulation of mood (Levitt & Joffe, op. cit.).

Abnormalities in cobalamin metabolism are often observed in cases of endocrine dysfunction. Serum cobalamin levels are significantly lower in patients with thyrotoxicosis than in controls, suggesting an increased metabolic need for cobalamin in the presence of high levels of thyroid hormone (Alperin et al., Blood 36, 632–641 (1970)). In animal models of thyrotoxicosis, cobalamin supplementation has been shown to counteract the impairment of oxidative phosphorylation and mitochondrial integrity caused by excess thyroid hormone (Kasbekar et al., Biochem. J. 72, 374–383 (1959)). A similar mutual antagonism has been demonstrated between cobalamin and corticosteroids. Thus, vitamin B12 administration counteracts a number of catabolic actions of cortisone in animals (Feng & Meites, Fed. Proc. 14, 47 (1955); Chemnitius, Int. Z. Vitaminforsch. 32, 386–391 (1962)), while experimentally induced cobalamin deficiency results in adrenocortical hypertrophy and elevated serum corticosteroids (Mgongo et al., Reprod. Nutr. Develop. 24, 845–854 (1984)). The latter study also revealed aberrations in gonadal steroid hormone levels consequent to cobalamin deficiency, an effect which may be related to the observed decline in serum B12 among users of estrogen-containing oral contraceptives (Mooij et al., Contraception 44, 277–288 (1991)).

Infertility in both males (Blair et al., Lancet 1, 49–50 (1968)) and females (Menachem et al., Am. J. Hematol. 46, 152 (1994)) has been noted in conjunction with cobalamin deficiency, with restoration of fertility commencing upon treatment with vitamin B12. Moreover, it has long been known that serum cobalamin levels tend to fall during pregnancy (Metz et al., Am. J. Hematol 48, 251–255 (1995)). Recently it has been suggested that a derangement of maternal homocysteine metabolism is responsible for some cases of reproductive disorders such as infertility, recurrent miscarriage and neural tube defects (NTD) (Steegers-Theunissen et al., Fertil. Steril. 60, 1006–1010 (1993)), and that periconceptional supplementation with vitamin B12 may be required for fully effective prophylaxis of NTD (Mills et al., Lancet 345, 149–151 (1995)). Congenital heart defects have been similarly linked with homocysteine embryotoxicity (Rosenquist et al., Proc. Natl. Acad. Sci. USA 93, 15227–15232 ( 1996)). An increased incidence of NTD and other malformations is also known to occur when drugs such as anticonvulsants are administered early in pregnancy; animal studies have demonstrated a role for cobalamin treatment in reducing the incidence of such birth defects (Mann & Gautieri, Lancet 1, 1451–1452 (1973); Elmazar et al., Fund. Appl. Toxicol. 18, 389–394 (1992)).

A novel application for cobalamin therapy is suggested by the finding that vitamin B12 deficiency is associated with increased risk of osteoporosis and bone fractures (Eastell et al., Clin. Sci. 82, 681–685 (1992); Goerss et al., J. Bone Miner. Res. 7, 573–579 (1992)). Marked reversal of bone loss upon treatment with a regimen incorporating cyanocobalamin has been noted (Melton & Kochman, Metabolism 43, 468–469 (1994)). Osteoporosis is also known to be induced by administration of thyroid hormone (Schneider et al., JAMA 271, 1245–1249 (1994)) and corticosteroids (Sambrook & Jones, Br. J. Rheumatol. 34, 8–12 (1995)). As discussed previously, hormone administration or endocrine hyperfunction can deplete cobalamins and, conversely, cobalamin treatment can normalize metabolic imbalances caused by some hormones. In view of these facts, cobalamin therapy is likely to be of use in preventing or reversing hormone-induced osteoporosis as well as the osteoporosis due to cobalamin malabsorption.

Immunodeficiency associated with cobalamin depletion, such as impaired antibody response to pneumococcal vaccine, has been studied in otherwise immunocompetent elderly patients with low serum cobalamin (Fata et al., Ann. Intern. Med. 124, 299–304 (1996)). Previous studies in patients with megaloblastic anemia have shown that immunoglobulin deficiency can resolve upon treatment with vitamin B12 (van Dommelen et al., Acta Med. Scand. 174, 193–200 (1963)). Decreases in suppressor T lymphocyte numbers among pernicious anemia patients have also been found, with one report indicating normalization of CD8+T-cell counts upon administration of hydroxocobalamin (Kubota et al., Am. J. Hematol. 24, 221–223 (1987)). Other impairments of immune function observed in cobalamin deficiency include defective chemiluminescence and bactericidal activity of neutrophils, with microbicidal activity returning to normal after treatment with vitamin B12 (Skacel & Chanarin, Br. J. Haematol. 55, 203–215 (1983)) or hydroxocobalamin (Seger et al., J. Inher. Metab. Dis. 3, 3–9 (1980)). The high incidence of tuberculosis among a vegetarian Indian population in England has been ascribed to defective macrophage killing secondary to dietary cobalamin deficiency, and it has been hypothesized that chronic cobalamin deficiency may particularly predispose individuals to infection by mycobacteria such as those causing tuberculosis and leprosy (Chanarin & Stephenson, J. Clin. Pathol. 41, 759–762 (1988)). The latter hypothesis may be relevant to the recently observed increased prevalence of tuberculosis among vulnerable populations worldwide, especially among those coinfected with HIV (Dolin et al., Bull. World Health Organ. 72, 213–220 (1994)). Thus, there appears to be a specific benefit for cobalamin supplementation in enhancing immunocompetence generally and in the treatment or prophylaxis of mycobacterial infection, of infections due to other microbial pathogens, and of opportunistic infections in AIDS.

Cobalamin deficiency appears to be common both in AIDS patients (Harriman et al., Arch. Intern. Med. 149, 2039–2041 (1989)) and in patients with asymptomatic HIV infection (Rule et al., Am. J. Hematol. 47, 167–171 (1994)); in either case cobalamin malabsorption or depletion has been shown to occur at a very early stage in HIV infection. Other researchers have established that whereas persistent cobalamin deficiency is associated with disease progression, normalization of serum cobalamin levels is associated with increased CD4+T-cell counts and improved AIDS index (a composite measure of disease progression) over time (Baum et al., AIDS 9, 1051–1056 (1995)). These findings suggest that cobalamin deficiency may have a pathogenic role in establishing HIV infection or in progression to AIDS, a supposition supported by the recent discovery that hydroxocobalamin, methylcobalamin and adenosylcobalamin are potent inhibitors of HIV infection in vitro (Weinberg et al., Blood 86, 1281–1287 (1995)). Demyelination, peripheral neuropathy, cognitive and affective changes and dementia are not uncommon consequences of HIV infection, and bear considerable resemblance to the neurological sequelae of chronic vitamin B12 deprivation. A relatively high prevalence of impaired B12 absorption or deficient serum cobalamin levels has been found among HIV-infected patients with neuropathy or myelopathy; the majority of those treated with cyanocobalamin reported a therapeutic response (Kieburtz et al. Arch. Neurol., 48, 312–314 (1991)). The reversal with vitamin B12 of an apparent advanced AIDS dementia complex has also been reported (Herzlich & Schiano, J. Intern. Med. 233, 495–497 (1993)), while measures of cognitive functioning have been directly correlated with serum cobalamin levels in HIV-infected patients (Shor-Posner et al., Arch. Neurol. 52, 195–198 (1995)).

Various cobalamins have shown efficacy in inhibiting tumor cell growth in culture, and in treating neoplasms and premalignant lesions in individuals. Pernicious anemia has been associated with an elevated risk of cancer, including melanoma, multiple myeloma, myeloid and other leukemias, and oral, pharyngeal and gastric cancers; the declining risk of leukemia and gastric carcinoma from the time of diagnosis of pernicious anemia is thought to result from therapy with vitamin B12 (Brinton et al., Br. J. Cancer 59, 810–813 (1989)). Deficiency of cobalamin and/or folate is believed to play a procarcinogenic role in general by impairing methionine synthesis, thereby inducing DNA hypomethylation (Herbert, in *Essential Nutrients in Carcinogenesis* (New York: Plenum Press, 1986), 293–311). Thus, dietary deficiency of methyl donors such as methionine and folate has been linked with increased risk of colorectal adenoma (Giovannucci et al., J. Natl. Cancer Inst. 85, 875–884 (1993)), and low serum cobalamin and folate levels have been correlated with a high incidence of esophageal carcinoma (EC) (Ran et al., Blood C, Suppl. 82, 532a (1993)). The latter authors have also shown that dietary supplementation with cobalamin and folate can correct esophageal dysplasia, the immediate precursor of EC, in cobalamin- and folate-deficient individuals. Similarly, smoking has been reported to induce a localized cobalamin deficiency in mucosal tissues (Piyathilake et al., FASEB 7, 713 (1993)), whereas treatment with vitamin B12 and folate has been shown to improve bronchial squamous metaplasia, a precursor of lung cancer, among smokers (Heimburger et al., JAMA 259, 1525–1530 (1988)). Moreover, when coadministered with folate, cobalamin has been reported to potentiate fluoropyrimidine antitumor activity (Tisman et al., Clin. Res. 33, 459A (1985)). There are also reports that cases of neuroblastoma (Bodian, Arch. Dis. Child. 38, 606–619 (1963)) and retinoblastoma (Horne, Am. J. Ophthalmol. 61, 910–911 (1966)) have responded to therapy with vitamin B12. In addition, studies conducted in vitro with the coenzyme forms of vitamin B12 have shown a cytotoxic effect of adenosylcobalamin on fast-growing malignant cell lines, with a lesser cytotoxicity induced by methylcobalamin (Tsao et al., Pathobiology 58, 292–296 (1990)); the cytotoxicity of adenosylcobalamin may be due to its inhibition of tRNA methylase activity, which is known to be elevated in tumor tissues (Tarasyavichene et al., Biokhimiya 41, 1614–1618 (1976)). These latter results suggest the existence of at least two distinct and independent mechanisms for the procarcinogenic effects of cobalamin deficiency.

Many of the aforementioned conditions associated with cobalamnin deficiency—e.g., AIDS, diabetes, atherosclerosis, apoptotic conditions, autoimmune and chronic inflammatory diseases, neurodegenerative conditions—are also associated with oxidative stress and/or antioxidant depletion. Cobalamin deficiency has itself been linked with alterations in redox status of endogenous antioxidants such as glutathione (GSH), ascorbic acid and reduced nicotinamide adenine dinucleotide (NADH). For example, elevated levels of oxidized GSH have been found in erythrocytes from untreated pernicious anemia patients, with improvement in redox status following upon treatment with vitamin B12 (Jocelyn, Biochem. J. 77, 363–368 (1960)). Similarly, an abnormally rapid oxidation of plasma ascorbic acid to dehydroascorbic acid has been noted in some cases of pernicious anemia, with the abnormality disappearing after cobalamin supplementation (Will et al., J. Lab. Clin. Med. 42, 967 (1953); Mueller and Will, Am. J. Clin. Nutr. 3, 30–44 (1955)). Other aberrations in ascorbic acid metabolism have also been observed in cobalamin deficiency (Cox et al., Clin. Sci. 17, 681–692 (1958)). Decreases in GSH (Register, J. Biol. Chem. 206, 705–709 (1954)), GSH reductase activity (Biswas & Johnson, Arch. Biochem. Biophys. 104, 375–380 (1964)) and in the ratio NADH/NAD (Chang et al., Fed. Proc. 16, 163–164 (1957)) have been found in livers of cobalamin-deficient animals. Thus, vitamin B12 appears to play a key role in maintaining antioxidants in their reduced state and/or in facilitating their proper metabolism. This conclusion may be generally relevant to the treatment of oxidative stress, inasmuch as oxidative stress can induce a functional cobalamin deficiency by oxidatively degrading the cobalamin molecule (e.g., via hydroxyl radical attack on the corrin ring) to yield toxic or inactive cobalamin analogues (Nazhat et al., J. Inorgan. Biochem. 36, 75–81 (1989)).

In particular, cobalamin supplementation alone or in combination with GSH may be beneficial in the treatment of oxidative stress associated with methylmercury intoxication, as has been demonstrated for various B complex vitamins and GSH (Sood et al., Cell. Mol. Biol. 39, 213–219 (1993)). Cobalamin may also be useful in the treatment of conditions characterized by both oxidative stress and glutamatergic excitotoxicity, such as diabetic retinopathy, macular degeneration and Batten's disease, among others (Agostinho et al., FASEB J. 11, 154–165 (1997)); a protective effect of cobalamin against glutamatergic excitotoxicity has been previously discussed (Yamamoto et al., op. cit.). Other conditions of impaired antioxidant homeostasis where cobalamin supplementation may be of use include cataract, heart disease (Harding et al., Biochem. Soc. Trans. 24, 881–883 (1996)) and also prolonged physical exercise (Reid et al., J. Cliln. Invest. 94, 2468–2474 (1994); Leeuwenburgh & Ji, Arch. Biochem. Biophys. 316, 941–949 (1995)). With or without the accompanying administration of antioxidants, cobalamin may be useful in inhibiting the muscle fatigue induced by prolonged exercise (Reid et al., op. cit.); indeed, studies conducted among ultraendurance athletes have revealed metabolic abnormalities suggesting an increased need for vitamin B12 in such athletes (Singh et al., Med. Sci. Sports Exerc. 25, 328–334 (1993)).

In addition to the various uses of cobalamin in treating conditions associated with cobalamin deficiency, cobalamins are effective in a number of applications regardless of whether any deficiency exists. Many of these applications stem from the avidity with which cobalamins scavenge, oxidize or otherwise interact with small bioactive molecules such as cyanide, nitric oxide, superoxide, carbon monoxide, sulfite and also with halogenated hydrocarbons. For example, hydroxocobalamin has long been known as an effective antidote for cyanide poisoning (Mushett et al., Proc. Soc. Exp. Biol. Med. 81, 234–237 (1952); Zerbe & Wagner, Crit. Care Med. 21, 465–467 (1993)). Recently it has been determined that cobalamins also interact with nitric oxide (Weinberg et al., Blood 84, 118a (1994)), and that hydroxocobalamin in particular attenuates the nitric oxide-dependent hypotension and mortality induced by septic shock (Greenberg et al., J. Pharmacol. Exp. Ther. 273, 257–265 (1995)). The latter authors suggest the use of hydroxocobalamin for treatment of sepsis, endotoxemia, systemic inflammatory response syndrome and other disorders associated with excess production of nitric oxide, as well as for adjunctive therapy when coadmninistered with inhaled nitric oxide or with nitric oxide donors. In addition to autoimmune disorders, chronic inflammatory disease, neurodegenerative disease and HIV infection, other conditions of nitric oxide toxicity which may be mitigated by cobalamins include migraine (Olesen et al., NeuroReport 4, 1027–1030 (1993)), stroke (Nowicki et al., Eur. J. Pharmacol. 204, 339–340 (1991)), viral pneumonia (Akaike et al., Proc. Natl. Acad. Sci. USA 93, 2448–2453 (1996)) and viral and bacterial neurological disease (Zheng et al., J. Virol. 67, 5786–5791 (1993); Koedel et al., Ann. Neurol. 37, 313–323 (1995)).

Similarly, a cobalamin complex with superoxide anion has been described (Bayston et al., J. Am. Chem. Soc. 91, 2775–2779 (1969)). Superoxide is a reactive oxygen species often coreleased with nitric oxide and implicated with it in the pathogenesis of AIDS and of various autoimmune, chronic inflammatory, ischemic and neurodegenerative diseases. With or without an accompanying release of nitric oxide, excessive production of superoxide has been linked with numerous pathologies, including infection by viral, bacterial, parasitic and fingal pathogens (Fuchs et al., Med. Hypotheses 36, 60–64 (1991)), induction of muscle wasting in cachexia (Buck & Chojkier, EMBO J. 15, 1753–1765 (1996)), photodamage to skin (Darr & Fridovich, J. Invest. Dermatol. 102, 671–675 (1994)), and the generation of clastogenic factors in a variety of illnesses. Clastogenic factors are low molecular weight chromosome-damaging agents which cause chromosome aberrations, sister chromatid exchanges, DNA strand breakage and gene mutation; their production is induced by superoxide and they in turn promote the formation of additional superoxide (Fuchs et al., Free Radic. Biol. Med. 19, 843–848 (1995)). Clastogenic factors have been implicated in the pathogenesis of gene mutations and/or malignancies associated with exposure to ionizing radiation, viruses, tumor-promoting chemicals, asbestos, herbicides such as paraquat, and with hereditary chromosome breakage syndromes such as ataxia telangiectasia, Bloom's syndrome and Fanconi's anemia (Emerit, Free Radic. Biol. Med. 16, 99–109 (1994)). All of the conditions cited represent targets for mitigation of superoxide toxicity by cobalamin.

Carbon monoxide, sulfites and various halogenated hydrocarbons also interact with cobalamin. Cobalamins have been reported to catalyze the oxidation of carbon monoxide to carbon dioxide (Bayston & Winfield, J. Catalysis 9, 217–224 (1967); Thauer et al., Eur. J. Biochem. 45, 343–349 (1974)) with potentially significant implications for the treatment of conditions associated with carbon monoxide production or exposure, such as smoking in adults and fetal growth retardation, sudden infant death syndrome (Hutter & Blair, Med. Hypotheses 46, 1–4 (1996)) and other pediatric conditions (Stevenson et al., J. Pediatrics 94, 956–958 (1979)). In addition, the neurotoxicity of carbon monoxide poisoning has been linked with excess nitric oxide production (Ischiropoulos et al., J. Clin. Invest. 97, 2260–2267 (1996)), which can be attenuated by hydroxocobalamin administration as previously noted. Cyanocobalamin is also known to be effective in the treatment of asthma in general (Crocket, Acta Allergol. 11, 261–268 (1957); Wright, Int. Clin. Nutr. Rev. 9, 185–188 (1989)) and in the suppression of allergic reactions to sulfites in cases of sulfite-sensitive asthma (SSA) in particular (Anibarro et al., J. Allergy Clin. Irnmunol. 90, 103–109 (1992)). The protective effect of vitamin B12 in non-SSA asthma may be due to the scavenging of nitric oxide by cobalamin, since excess production of nitric oxide is known to be involved in asthmatic inflammation (Lundberg et al., Nature Med. 3, 30–31 (1997)). In contrast, the protective effect of cyanocobalamin in SSA is presumed to be a consequence of the extracellular nonenzymatic oxidation of sulfite catalyzed by cobalamins (Jacobsen et al., J. Allergy Clin. Immunol. 73, 135 (1984)). Finally, vitamin B12 has been shown to mediate the dehalogenation of various halogenated pesticides (Schrauzer & Katz, Bioinorg. Chem. 9, 123–143 (1978)), environmental toxins (Assaf-Anid et al., Appl. Env. Microbiol. 58, 1057–1060 (1992)) and solvents (Krone et al., Biochemistry 30, 2713–2719 (1991)), a result which may account for the protection afforded by vitamin B12 in carbon tetrachloride-induced hepatic injury (Kasbekar et al., Biochem. J. 72, 384–389 (1959)).

Other applications for cobalamins include treatment of dermatitis (Simon, J. Allergy 22, 183–185 (1951)); antagonism of histamine (Ata, in *Vitamin B12 und Intrinsic Factor* (Stuttgart: Ferdinand Enke Verlag, 1957), 544–553); treatment of oversedation due to intoxication with sedatives and/or alcohol (Newbold, Med. Hypotheses 30, 1–3 (1989)); treatment of anorexia nervosa (Korkina et al., Zhur. Nevropat. Psikhiat. 89, 82–87 (1989)); relief of fatigue (Ellis & Nasser, Br. J. Nutr. 30, 277–283 (1973)); enhancement of choline and acetylcholine biosynthesis (Sasaki et al., Pharmacol. Biochem. Behav. 43, 635–639 (1992)); treatment of sleep disturbances and "jet lag" by re-entrainment of circadian rhythms (Honma et al., Experientia 48, 716–720 (1992)); treatment of viral conditions such as hepatitis (Kelemen et al., Int. Z. Vitaminforsch. 31, 307–316 (1961)), poliomyelitis (Leroy & Robin, Semaine hop. Paris 31, 1097–1098 (1955)), and herpetic lesions (King, N.Z. Med. J. 105, 135 (1992)); potentiation of immunomodulation when coadministered with interferon (Medenica et al., Blood 86, Suppl. 1, 850a (1995)); pain relief (Surtees & Hughes, Lancet 1, 439–441 (1954); Leuschner, Arzneim.-Forsch./Drug. Res. 42, 114–115 (1992)); treatment of osteoarthritis (Flynn et al., J. Am. Coll. Nutr. 13, 351–356 (1994)); promotion of epithelial cell growth (Ansell, Lancet 2, 994 (1962)), of wound healing (Findlay, Proc. Soc. Exp. Biol. Med. 82, 492–495 (1953)) and of recovery of cardiac muscle in myocardial infarction (Nikolaeva et al., Circ. Res. 35, Suppl. III, 202–213 (1974)); detoxification of poisoning caused by heavy metals such as cadmium (Couce et al. J. Inorg. Biochem. 41, 1–6 (1991)), lead (Kleinsorge et al., Zschr. inn. Med. 9, 903–906 (1954)) and mercury (e.g., methylmercury, Sood et al., Cell. Mol. Biol. 39, 213–219 (1993)) and non-metals such as selenium (Chen & Whanger, Toxicol. Appl. Pharmacol. 18, 65–72 (1993)); antagonism of convulsions and mortality caused by various agents and medications (Ata, in *Vitamin B12 und Intrinsic Factor* (Stuttgart: Ferdinand Enke Verlag, 1957), 544–553) and treatment of febrile convulsions (Osifo et al., J. Neurol. Sci. 68, 185–190 (1985)).

Corrinoids are cobalamin analogs which are used in lieu of cobalamin by certain microorganisms. Generally, corrinoids differ from cobalamins only in an alteration of the dimethylbenzimidazole moiety found in all true cobalamins. Corrinoids are believed to be inactive in eukaryotic cells, and there is evidence that corrinoids may actually antagonize some functions of vitamin B12 or otherwise interfere with cobalamin uptake or metabolism in humans and animals. Both cobalamins and corrinoids may nevertheless be useful in eukaryotes or, e.g., as growth factors, prebiotics or essential nutrients for microorganisms of value, such as those employed in fermentation reactions or in environmental detoxification, for example.

SUMMARY OF THE INVENTION

The invention pertains to a novel composition of cobalamin which results in increased cellular uptake of cobalamin. The composition comprises a mixture in a physiologically acceptable carrier of three components: cobalamin; one or more amino acids selected from Group I (defined below); and one or more amino acids selected from Group II (defined below). Group I consists of basic or positively charged amino acids, such as lysine, arginine, (protonated) histidine and ornithine. Group II consists of uncharged amino acids with side chains incorporating at least one heteroatom (preferably capable of hydrogen-bonding), such as glutamine, asparagine, tyrosine, tryptophan, histidine, methionine, cysteine, hydroxyproline, serine and threonine. Preferably, the group I amino acid and the group II amino acid are different amino acids. A preferred composition comprises cobalamin, lysine and glutamine in a molar ratio of about 1:2:4. The composition of the invention can be administered to an animal or an individual to provide increased cellular uptake of cobalamin. The composition optionally includes a microorganism; in preferred embodiments, the microorganism is capable of catalyzing the formation of a cobalamin:amino acid complex. The composition provides an effective means of treating those conditions for which cobalamin is presently administered. For example, the composition can be used to treat cobalamin deficiencies, neuropathies and demyelinating conditions. The composition can also be used in humans and animals to treat sensitivity to sulfites, stimulate choline biosynthesis, enhance immunocompetence, ameliorate nitric oxide and superoxide toxicity, promote healing of wounds, sores and other lesions, treat osteoarthritis, relieve fatigue, induce analgesic and anti-inflammatory effects, detoxify poisoning due to certain elements, treat convulsions, and adjust circadian rhythms. The composition can also be utilized as an agent in certain biomedical or biotechnological applications, e.g., as a growth factor for eukaryotic cells in culture. In a further application, the scope of the invention is intended to encompass compositions of certain cobalamin analogs (corrinoids) with amino acids selected from Groups I and II as defined above, with a preferred composition comprising corrinoid, lysine and glutamine in a ratio of about 1:2:4. Compositions involving cobalamins or corrinoids may be used as growth factors or prebiotics for microorganisms of value, e.g., those used in fermentation reactions. Such compositions may also be used to promote the environmental detoxification of halogenated pesticides, solvents and related substances by various microorganisms.

Thus, in one embodiment, the invention provides a composition comprising a mixture of: a corrin selected from the group consisting of cobalamins and corrinoids; a first amino acid having a side chain which includes a basic or positively charged moiety; and a second amino acid with an uncharged side chain which includes at least one heteroatom, wherein the composition comprises an excess by weight of the corrin relative to at least one of the first amino acid and the second amino acid. The corrin can be a cobalamin. The first amino acid can be selected from the group consisting of lysine, arginine, histidine, and ornithine. The second amino acid can be selected from the group consisting of glutamine, asparagine, tyrosine, tryptophan, histidine, methionine, cysteine, hydroxyproline, serine and threonine. The corrin can be present in a ratio by weight of at least 2:1 relative to the first amino acid. The composition can further include a pharmaceutically acceptable carrier.

In another embodiment, the invention provides a composition comprising a mixture of a cobalamin; a first amino acid selected from the group consisting of lysine, arginine or ornithine; and a second amino acid selected from the group consisting of glutamine, tyrosine, serine, threonine, tryptophan or asparagine, wherein the composition comprises an excess by weight of the cobalamin relative to at least one of the first or second amino acid. The first amino acid can be lysine and the second amino acid can be glutamine.

In another embodiment, the invention provides a composition comprising a mixture in a pharmaceutically acceptable carrier of: cobalamin; lysine, arginine or ornithine; and glutamine, tyrosine, serine, threonine, tryptophan or asparagine, in a molar ratio of from about 1:0.1:0.1 to about 1:100:100. The composition can include cobalamin, lysine and glutamine in a molar ratio of about 1:2:4. Alternatively, the composition can include cobalamin, lysine, glutamine and tyrosine in a molar ratio of about 1:2:2:2. The composition can further include a microorganism capable of catalyzing the formation of a cobalamin:amino acid complex.

In another aspect, the invention provides a method of increasing cellular uptake of cobalamin in the cells of a subject, comprising administering to the subject an active amount of a composition comprising a mixture of: cobalamin; lysine, arginine or ornithine; and glutamine, tyrosine, serine, threonine, tryptophan or asparagine, in a molar ratio of from about 1:0.1:0.1 to about 1:100:100, such that cellular uptake of cobalamin in the cells of the subject is increased. The composition can include a pharmaceutically acceptable carrier.

In another aspect, the invention provides a method for treating a condition associated with cobalamin deficiency in a subject. The method includes the steps of administering to a subject in need thereof a therapeutically effective amount of a composition comprising a mixture in a pharmaceutically acceptable carrier of: cobalamin; lysine, arginine, histidine or ornithine; and glutamine, tyrosine, serine, threonine, tryptophan or asparagine; in a molar ratio of from about 1:0.1:0.1 to about 1:100:100, such that a condition associated with cobalamin deficiency in the subject is treated. The subject can be a human, and the condition can be, e.g., Alzheimer's disease or a condition associated with retroviral infection, including HIV infection.

DETAILED DESCRIPTION

The present invention is directed to a composition of cobalamin or related corrinoid which results in enhanced transport of cobalamin or corrinoid into cells. As defined herein, the term cobalamin refers to vitamin B12 in any of its biologically active forms, including cyanocobalamin, hydroxocobalamin, methylcobalamin and adenosylcobalamin. The term corrinoid refers to any of the cobalamin analogues which may be utilized by microorganisms in lieu of cobalamin. The term "corrin," as used herein, refers to a cobalamin or corrinoid as described herein.

To form the composition of the invention, cobalamin or corrinoid is combined with two amino acid components. The term "amino acid" is art-recognized, and, as used herein, refers to both naturally-occurring and synthetic amino acids. Unless otherwise specified, the term "amino acid" includes all stereoisomers of the amino acid. However, in preferred embodiments, at least one of the first and second amino acids (more preferably both) are of the L-form, which is the form of naturally-occurring amino acids that is most common in nature. The first amino acid component is selected from the group of amino acids having a side chain which includes a basic or positively charged moiety, referred to herein as Group I, which includes lysine, arginine, histidine (e.g., in its protonated form), and ornithine. Modified forms of naturally-occurring amino acids, e.g., hydroxylysine or homoarginine, are within the scope of the invention, so long as the amino acid side chain is basic or positively charged. Similarly, synthetic or synthetically-modified amino acids are also contemplated for use in the compositions (and methods) of the invention. A particularly preferred first amino acid component for forming a composition of the invention is lysine.

A second amino acid component of the composition is selected from the group of amino acids with uncharged side chains incorporating at least one heteroatom, referred to herein as Group II. Thus, Group II includes the amino acids glutamine, asparagine, tyrosine, tryptophan, histidine, methionine, cysteine, hydroxyproline, serine and threonine. Modified forms of these amino acids which maintain the neutrality of the molecule and which incorporate at least one heteroatom per side chain can also be used in the composition, e.g., isoglutamine or DOPA. Glutamine is a preferred second amino acid component for use in the composition.

The composition of the invention is formed by combining a cobalamin or corrinoid with at least one amino acid selected from each of Group I and Group II as described above. It is not necessary that only one amino acid from each group be used to form the composition. For example, the composition may be formed by combining a cobalamin or corrinoid with lysine as a first amino acid component and a combination of glutamine and tyrosine as a second amino acid component. As a further example, lysine and arginine can be included as a first amino acid component and glutamine as a second amino acid component.

In certain embodiments, a composition of the invention can be formulated by dissolving a mixture of the three components, i.e., cobalamin or corrinoid, a first amino acid component and a second amino acid component, in an appropriate vehicle such as distilled (preferably deoxygenated) water to form a solution. The composition includes an actual weight of cobalamin or corrinoid sufficient to provide a therapeutically or biologically active amount, typically in the range from 1 $\mu$g to 1000 $\mu$g per dose. In certain embodiments, the cobalamin or corrinoid can be present in excess (by weight) over the first and/or the second amino acid components, e.g., in a ratio by weight of at least 2:1 relative to the first amino acid and/or the second amino acid. As an example, a typical composition may be formed by combining 1 gram of cobalamin or corrinoid (e.g., cyanocobalamin), 250 mg of a first amino acid component (e.g., lysine) and 250 mg of a second amino acid component (e.g., glutamine) in a suitable volume of distilled water (e.g., 1 liter).

The amount of each component in the composition can also be expressed in terms of molar ratios. For example, a molar ratio of cobalamin or corrinoid to the first and second amino acid components can range from about $1:10^{-4}:10^{-4}$ to about $1:10^7:10^7$, more preferably $1:10^{-2}:10^{31\ 2}$ to about $1:10^3:10^3$. A preferred composition includes cobalamin or coriinoid, a first amino acid component and a second amino acid component in a molar ratio of about 1:2:4. A particularly preferred composition comprises cobalamin or corrinoid, lysine and glutamine in a molar ratio of about 1:2:4. Once the components are dissolved in the distilled water, the solution can be stored under sterile conditions for a period of time sufficient to permit the ingredients to interact, e.g., three weeks. Without wishing to be bound by any theory, the inventors believe that the cobalamin or corrinoid forms a non-covalent complex with the first and second amino acid components, and that the complex forms over a period of time. It will be understood that the time required can vary depending upon factors such as temperature, concentration of the ingredients, and the like. The complex-formation time is believed to vary, e.g., in the range of about 30 minutes to about four weeks. Thus, in one aspect, the invention provides a non-covalent complex of cobalamin or corrinoid, a first amino acid component and a second amino acid component in a molar ratio of about 1:2:4. The first and second amino acid components can be of group I and group II, respectively, as described above. The resulting composition can then be utilized directly, combined with additional ingredients such as vitamins and minerals (e.g., soluble salts of divalent cations such as calcium, magnesium, manganese, copper, zinc, and ferrous iron), diluted further, and/or crystallized or dried to yield the composition in solid form.

In preferred embodiments, at least one of the components (e.g., cobalamin, Group I or Group II amino acid) is provided in a substantially purified form. In a particularly preferred embodiment, at least two components (i.e., at least two of the cobalamin or corrinoid, Group I amino acid, and Group II amino acid) are provided in substantially purified form. In certain embodiments, the cobalamin or corrinoid, Group I amino acid, and Group II amino acid, can all be provided in substantially purified form. A "substantially purified" material is one which has been substantially purified, isolated, or freed from inactive or interfering substances.

Additional compositions of the invention can be formulated by administering the components—i.e., cobalamin or corrinoid, a first amino acid component and a second amino acid component—to various living organisms which can, in preferred embodiments, catalyze the formation of a cobalamin:amino acid complex. Examples of organisms which can be utilized for this purpose include lactobacilli, cyanobacteria, algae, fungi such as yeasts and mushrooms, and symbiotes of these such as kombucha (a fungal/bacterial symbiote); the preceding list is meant to be illustrative and not exhaustive. The components of the invention can be added to the media of microorganisms in culture, and the microorganisms harvested after a period of time sufficient to ensure uptake of the components. For example, the cobalamin or corrinoid components and the first and second amino acid components can be added to the culture media of cyanobacteria or microalgae such as Chlorella or Spirulina, and the enriched microorganisms harvested for drying, for preparation of tinctures and extracts, and for other purposes. As another example, the components of the invention can be added to milk or milk products to produce yoghurt after inoculation with lactobacilli or other bacteria; once fermentation is complete (typically 4 to 12 hours) the yoghurt may be consumed, stored or dried (e.g., spray-dried or lyophilized) to yield a dried composition enriched in the cobalamin compositions of the invention. Yoghurt produced in this way may be ingested for its therapeutic benefit, and also applied topically (e.g., in the form of yoghurt masks) for cosmetic purposes and/or skin rejuvenation.

Similar fermentations can be carried out using the components of the invention in combination with inoculation by microorganisms of various fermentable substrates, such as those derived from dairy, soy, grain, fruit, vegetable and other sources. Foods which may be enriched in this manner include dairy products such as yoghurts, cheeses and buttermilk, the soy equivalents of these, breads and grain products prepared with yeasts or sourdough cultures, tempeh (a fermented soy bean product), and the like. In each case a quantity of cobalamin or corrinoid sufficient to provide a therapeutically or biologically active amount can be added to the fermentable substrate and/or inoculum; typical amounts to be added range from about 1 $\mu$g to about 1000 $\mu$g cobalamin or corrinoid per seving of bread, yoghurt or other product.

A further composition of the invention can be formulated by mixing the components—i.e., cobalamin or corrinoid and the first and second amino acid components—with dried live microorganisms such as lactobacilli. The resulting mixture can be ingested for therapeutic benefit, e.g., in capsules or in powdered form added to food. Typically a unit dose of such a mixture will contain from 50,000 to 50 billion active microorganisms at time of manufacture, more preferably from 500,000 to 10 billion microorganisms, together with cobalamin or corrinoid in a range of 1 µg to 100 mg, more preferably in a range of 10 µg to 10 µg, and with amino acids from Group I and Group II in a range of 1 µg to 10 grams each, more preferably in a range of 1 mg to 1 gram each. Prebiotics such as fructooligosaccharides may also be added. In a particularly preferred composition of the invention, a unit dose comprises about 500 million each L. acidophilus and L. bifidus, about 400 µg of cyanocobalamin, about 200 mg of glutamine and about 50 mg of lysine (as the free base, or, e.g., about 62.5 mg lysine as the monohydrochloride), all of which may be encapsulated together in a standard #0 gelatin capsule. For bumans, a therapeutic dosage of the preferred composition typically ranges from 1 to 10 such unit doses per day; for animal use, the human therapeutic dose may be scaled as required in an obvious fashion according to the relative size or body mass of the animal.

In general, if microorganisms are administered to the subject, the microorganisms are preferably in a solid form (e.g., dried), and are preferably in an orally available form.

When formulated with cobalamin, the composition of the invention has demonstrated enhanced transport of cobalamin, e.g., from serum into cells, relative to cobalamin in the absence of the amino acid components of the mixture. It is therefore expected that the composition thus formulated will be significantly more effective than cobalamin alone in all applications for which cobalamin has been found or is believed to be useful, including the treatment of all forms of cobalamin deficiency.

As is described in detail herein, the compositions of the invention are useful for treatment of a variety of conditions. As used herein, the term "subject" refers to a warm-blooded animal, more preferably a mammal, including humans and non-human mammals including cats, dogs, mice, rats, horses, sheep, pigs, primates including monkeys, and the like. As further described herein, a subject can be suffering from a recognized cobalamin deficiency, or can be affected by a condition which can be treated by administration of the compositions of the invention, even though no cobalamin deficiency has been recognized or diagnosed in the subject. The term "treating" refers to partial or total amelioration of symptoms, partial or total prevention, inhibition or delay of the development or progress of the condition, partial or total prevention, inhibition or delay occurrence of new symptoms (e.g., by delaying the onset of a condition or symptoms of a condition), and the like.

Typical cobalamin deficiency is caused by malnutrition or malabsorption, and is common among the elderly, among vegetarians, in malnourished populations generally, and among patients who have undergone gastrointestinal surgery or who suffer from chronic intestinal disease. Cobalamin deficiency can also be induced by long term therapy with certain stomach-acid suppressing medications and by exposure to nitrous oxide, a commonly used anesthetic gas. More rarely, cobalamin deficiency may also result from congenital lack of the carrier protein transcobalamin II (TC II). Whether due to malnutrition, malabsorption, lack of TC II or other causes, untreated cobalamin deficiency may result in hematological abnormalities such as megaloblastic anemia, and may be associated with peripheral neuropathy, myelopathy and neuropsychiatric disorders as well. Subsequent studies have determined the existence of other types of cobalamin deficiency, variously referred to as atypical, cryptic or subtle, which are occasionally found associated with malabsorption of food-bound cobalamin. An atypical, cryptic or subtle cobalamin deficiency can exist in an individual despite normal or minimally depressed serum cobalamin concentrations, few or no hematologic abnormalities, and no indication of the absence of intrinsic factor (Lindenbaum et al., N. Engl. J. Med. 318, 1720–1728 (1988); Cannel et al., J. Lab Clin. Med. 109, 454–463 (1987)). Like typical cobalamin deficiency, atypical, cryptic or subtle forms of cobalamin deficiency can also be treated by administration of the composition of the invention.

Typical cobalamin deficiency is generally detected by assaying for low serum levels of cobalamin, detecting hematologic abnormalities (i.e., macrocytosis, hypersegmentation of neutrophil nuclei, and recognizable megaloblastic changes in the bone marrow), or detecting the absence of metabolic factors (i.e., using the Schilling test to infer a deficiency of intrinsic factor). A number of assays have been developed which can detect atypical, cryptic or subtle cobalamin deficiency. The deoxyuridine suppression test (dUST) has been used to detect atypical cobalamin deficiency in persons with low serum cobalamin levels but no apparent hematological abnormalities (Carmel et al., J. Lab. Clin. Med. 109, 454–463 (1987)). Assays for serum levels of methylmalonic acid and total homocysteine have also been used to detect cobalamin deficiency, particularly in persons with few or no hematologic abnormalities, normal results on the Schilling test, or normal or minimally depressed serum cobalamin levels (Lindenbaum et al., N. Engl. J. Med. 318, 1720–1728 (1988)). Other tests which can be applied to detect atypical, cryptic or subtle cobalamin deficiency include measurement of holo-TC II levels (Das et al., J. Nutr. Biochem. 2, 455–464 (1991)), assessment of functional nutritional status via lymphocyte culture (Shive, J. Int. Acad. Preventive Med. 8, 5–16 (1984)), detection of elevated levels of 2-methylcitric acid I and II in serum, urine or CSF (Allen et al., Metabolism 42, 978–988 (1993)), and measurement of absorption of radiolabeled food-bound cobalamin by whole-body counting (Miller et al., Am. J. Hematol. 44, 211–212 (1993)). The composition and method of the present invention is directed at all forms of cobalamin deficiency, whether typical, atypical, subtle or cryptic, whether determined by macrocytosis or other hematological abnormality, by neuropsychiatric or neurological signs, by low cobalamin levels in serum, cerebrospinal fluid, other fluids or various tissues, by congenital, metabolic or other deficiency of individual cobalamin congeners in various fluids and tissues, by impaired absorption of radiolabeled cobalamin, by high levels of serum, urinary or CSF methylmalonic acid, homocysteine, or 2-methylcitric acids I and II, by abnormal responses to the deoxyuridine suppression test, by elevated levels of apo-transcobalamin II or low levels of holo-transcobalamin II, by elevated levels of toxic or inactive cobalamin analogues, by assay of functional nutritional status of cells in culture, or by any other means. Moreover, the composition of the invention is also directed toward the treatment of cobalamin deficiency secondary to all forms of cobalamin malabsorption, whether caused by hypochlorhydria, gastritis or gastrectomy, by deficiency of intrinsic factor, autoimmune blockade of intrinsic factor or any other defect in the uptake, transport or release of cobalamin by intrinsic factor, by pancreatic insufficiency or other defect of pancreatic enzyme activity, by gastroenteropathy of any kind, by ileal resection, by deficiency, blockade or other defect of intrinsic factor receptors, by deficiency of transcobalamnin II, by any defect in cobalamin uptake, transport or release by transcobalamins, by deficiency, blockade or other defect of transcobalamin receptors, by any defect of lysosomal proteolysis of transcobalamins, or by any other means.

Another application to which the composition of the invention can be directed is in the treatment of a number of diseases and disease states which have been characterized by or associated with some form of cobalamin deficiency. As discussed previously, macrocytic anemia is a well known consequence of cobalamin deficiency which is readily treatable with cobalamin and therefore with the composition of the invention. Cobalamin deficiency may also be common among sickle cell disease (SCD) patients (Carmel & Johnson, Blood 86 Suppl. 1, 644a (1995); Al-Momen, J. Intern. Med. 237, 551–555 (1995)), where the anemia of SCD may mask a coexisting cobalamin deficiency anemia and where homocysteine levels may be elevated (Lowenthal et al., Blood 88, Suppl. 1, 492a (1996)). Another condition unexpectedly associated with aberrant cobalamin metabolism is iron deficiency anemia, where an increased unsaturated B12 binding capacity (UBBC) has been found (Rosner & Schreiber, Am. J. Med. Sci. 263, 473–480 (1972)). Delayed plasma clearance of radiolabeled vitamin B12 in iron deficiency anemia may be a consequence of decreased uptake of vitamin B12 by tissues as a result of diminished eytropoeisis (Cook & Valberg, Blood 25, 335–344 (1965)). Because of the known role of erythrocytes in delivering cobalamin and other vitamins to tissues (Sorrell et al., Am. J. Clin. Nutr. 24, 924–929 (1971)), one may conclude that any anemia associated with diminished erythropoiesis and/or low erythrocyte counts can induce a state of functional cobalamin deficiency. Moreover, some anemias are caused by or associated with folate deficiency; folate supplementation in the absence of cobalamin is known to exacerbate the neuropathology of cobalamin deficiency. The composition of the present invention is therefore directed to the treatment of all forms of anemia associated with cobalamin deficiency, diminished erythropoiesis and/or low erythrocyte counts, and especially to the treatment of anemias complicated by coexisting folate deficiency, such as SCD (Carmel & Johnson, op. cit.) and thalassemia (Kumar et al., Am. J. Clin. Pathol. 84, 668–671 (1985)).

Treatment with cobalamin, and therefore with the composition of the invention, may be beneficial in conditions associated with elevated levels of apo-transcobalamin II, such as Gaucher's disease (Gilbert & Weinreb, N. Engl. J. Med. 295, 1096–1101 (1976)) and also autoimmune conditions (Frater-Schroder et al., Lancet 2, 238–239 (1978); Gimsing et al., Scand. J. Rheumatol. 11, 1–4 (1982)). Autoimmune disorders treatable with cobalamin, and therefore with the composition of the invention, include rheumatoid arthritis (Vreugdenhil et al., Ann. Rheum. Dis. 49, 93–98 (1990); Yamashiki et al., J. Clin. Lab. Immunol. 37, 173–182 (1992)), multiple sclerosis (Reynolds et al., Arch. Neurol. 48, 808–811 (1991); Kira et al., Intern. Med. 33, 82–86 (1994)), vitiligo (Montes et al., Cutis 50, 39–42 (1992)), psoriasis (Stingily, Miss. Doctor 32, 222–223 (1955)) and lupus erythematosus (Molad et al., Am. J. Med. 88, 141–144 (1990); Stingily, Miss. Doctor, op. cit.), among others.

Other conditions treatable with cobalamin, and therefore with the compositions of the invention, include disorders of carbohydrate metabolism such as diabetes mellitus (Takahashi et al., Diabetes Res. Clin. Pract. 25, 13–17 (1994); Ralli et al., J. Clin. Endocrinol. Metab. 15, 898 (1955)), glucose intolerance of various etiologies (Hadnagy et al., Int. Z. Vitaminforsch. 33, 141–150 (1963)), alcoholism (Dobbins, U.S. Pat. No. 4,918,102 (4/17/90); Kanazawa & Herbert, Lab. Invest. 53, 108–110 (1985)), cystic fibrosis (Hardin et al., Diabetes 44, Suppl. 1, 200A (1995); Lindemans et al., Acta Paediatr. Scand. 74, 795–796 (1985)), and the disorder of insulin resistance referred to as Syndrome X (leaven, Diabetes 37, 1595–1607 (1988); Jackson, Diabetes Care 13, Suppl. 2, 9–19 (1990)), which is associated with Type II diabetes, hypertension, obesity, coronary artery disease and age-related glucose intolerance. Atherosclerosis including coronary artery disease may be generally amenable to treatment with the composition of the invention (Nath & Saikia, Arch. Biochem. Biophys. 79, 216–233 (1959); Olszewski et al., Atherosclerosis 75, 1–6 (1989); Olszewski et al., ibid. 88, 97–98 (1991)), as may other disorders of lipid and/or homocysteine metabolism. In particular, the composition of the invention is applicable to the treatment of homocysteine-related vascular occlusive disease such as diabetic retinopathy (Neugebauer et al., Lancet 349, 473–474 (1997)) and arterial and venous thrombosis (Harpel et al., J. Nutr. 126, 1285S–1289S (1996)).

A further application of the composition of the invention is in the treatment of various neuropathies and demyelinating conditions related to cobalamin deficiency. Administration of cobalamin, and therefore of the composition of the invention, may be effective against diseases and disease states characterized by or associated with neuropathy, such as diabetic neuropathy (Tanaka et al., in *Diabetic Neuropathy* (Amsterdam: Excerpta Medica, 1982), 114–119); Yaqub et al., Clin. Neurol. Neurosurg. 94, 105–111 (1992)), AIDS-related neuropathy (Kieburtz et al., Arch. Neurol. 48, 312–314 (1991)), uremic neuropathy (Taniguchi et al., Clin. Ther. 9, 607–614 (1987)), leprous neuropathy and the deficiency neuropathy of pellagra (Bedi et al., J. Assoc. Physicians India 21, 473–479 (1973)), Lebere's hereditary optic neuropathy (Rizzo, Neurology 45, 11–16 (1995)) and other cases of optic neuritis (Heaton, Proc. Nutr. Soc. 19, 100–105 (1960)), as well as certain instances of tinnitus (Shemesh et al., Am. J. Otolaryngol. 14, 94–99 (1993)) and orthostatic hypotension (Lossos & Argov, J. Am. Geriatr. Soc., 39, 601–602 (1991)). Similarly, demyelinating conditions resulting from cobalamin deficiency may be more effectively treated with the composition of the invention, as may a number of diseases or disease states which are characterized by or associated with demyelinating conditions. These diseases or disease states include the myelopathies associated with AIDS (Kieburtz et al., Arch. Neurol. 48, 312–314 (1991)), multiple sclerosis (Reynolds et al., Arch. Neurol. 48, 808–811 (1991); Kira et al., Intern. Med. 33, 82–86 (1994)), and certain postinfectious and postvaccinal neuropathies such as Guillain-Barre syndrome and viral encephalomyelitis, for which experimental allergic neuritis and experimental allergic encephalomyelitis are animal models (Inada et al., in *Vitamin B12* (Berlin: Walter de Gruyter & Co., 1979), 1017–1018).

Cobalamin is known to play an important role in maintaining mitochondrial integrity (Reddi & Nath, J. Vitaminol. 17, 101–104 (1971)) and, conversely, cobalamin deficiency is thought to be a metabolic trigger which can precipitate the symptomatology of mitochondrial disease (Rizzo, Neurology 45, 11–16 (1995)). In view of these facts, the composition of the invention can also be applied to the treatment of mitochondrial disorders and other deficiencies of cellular bioenergetics, including apoptotic conditions (Richter et al., FEBS Lett. 378, 107–110 (1996)), hypoxia/ischemia and various neurodegenerative diseases (Davolio & Greenamyre, Neurosci. Lett. 192, 29–32 (1995); Beal, Ann.

Neurol. 38, 357–366 (1995)). Indeed, cobalamin deficiency has often been found in conjunction with primary degenerative dementia such as Alzheimer's (Karnaze & Carmel, Arch. Intem. Med. 147, 429–431 (1987)), and effective treatment with cobalamin has been reported (Ikeda et al., Clin. Ther. 14, 426–437 (1992)). Similarly, Down's syndrome, which eventually manifests a neuropathology indistinguishable from that of Alzheimer's, is associated with cobalamin deficiency (Howell et al., Scand. J. Haemat. 11, 140–147 (1973)) and may be treated effectively with a regimen incorporating cobalamin (Harrell et al., Proc. Natl. Acad. Sci. USA 78, 574–578 (1981)). Cobalamin may also be effective in treating vascular dementia, as judged from studies conducted with an animal model (Minami et al., Biogenic Amines 8, 33–52 (1991)). Other neurodegenerative conditions have also been associated with cobalamin deficiency (Bauer & Heinrich, in *Vitamin B12 und Intrinsic Factor* (Stuttgart: Ferdinand Enke Verlag, 1957), 499–509) or have been reported to be ameliorated by cobalamin therapy (Levin, Am. J. Digest. Dis. 22, 96–97 (1955)). The composition of the present invention is therefore directed to the treatment of neurodegenerative conditions including amyotrophic lateral sclerosis and Alzheimer's, Down's, Parkinson's and Huntington's diseases, as well as to the treatment of any form of glutamatergic excitotoxicity (Yamamoto et al., Eur. J. Pharmacol. 281, 335–340 (1995)) or mitochondrial dysfunction (Beal, Ann. Neurol. 38, 357–366 (1995)) which may underlie these conditions.

In another application, the composition of the invention can be used to treat cognitive, affective, psychological and psychiatric disturbances associated with cobalamin deficiency (Lindenbaum et al., N. Engl. J. Med. 318, 1720–1728 (1988)), including obsessive-compulsive disorder (Hermesh et al., Acta Psychiatr. Scand. 78, 8–10 (1988)), attention deficit disorder (Robin, Semaine hop. Paris 30, 4129–4132 (1954)) and related conditions of learning disability coupled with aggressive behavior (Schrauzer et al., Biol. Tr. Element Res. 34, 161–176 (1992)). The present composition may also be beneficial in treating schizophrenia (Regland et al., J. Neural Transm. 98, 143–152 (1994); Joshi et al., J. Orthomol. Psychiatry 9, 35–40 (1980)), AIDS-related dementia (Herzlich & Schiano, J. Intern. Med. 233, 495–497 (1993)) and AIDS-impaired cognitive functioning (Shor-Posner et al., Arch. Neurol. 52, 195–198 (1995)).

In yet another application, the composition of the invention may be used to treat endocrine dysfunctions related to cobalamin deficiency, such as thyrotoxicosis (Alperin et al., Blood 36, 632–641 (1970); Kasbekar et al., Biochem. J. 72, 374–383 (1959)) and excessive production of corticosteroids (Mgongo et al., Reprod. Nutr. Develop. 24, 845–854 (1984); Feng & Meites, Fed. Proc. 14, 47 (1955)). In particular, the antagonism by cobalamin of various steroidal effects suggests the use of the composition of the invention in the treatment of chronic stress, where corticosteroid levels are generally elevated. Cobalamin, and therefore the composition of the present invention, may also be usefull in the treatment of hypocorticism when coadministered with steroids (Ferrutti & Speranza, Minerva Ginecol. 34 619–623 (1982)). Moreover, the composition of the invention is also directed to the treatment of osteoporosis associated with cobalamin deficiency (Melton & Kochman, Metabolism 43, 468–469 (1994); Kim et al., Metabolism 45, 1443–1446 (1996)), whether or not such deficiency is accompanied by endocrine dysfunction or excessive administration of hormones.

In a further application, the composition of the invention is applicable to the treatment of infertility in both males (Blair, Lancet 1, 49–50 (1968)) and females (Menachem et al., Am. J. Hematol. 40, 152 (1994)), and to the treatment of reproductive disorders such as recurrent miscarriage (Steegers-Theunissen et al., Fertil. Steril. 60, 1006–1010 (1993)), neural tube defects (Mills et al., Lancet 345, 149–151 (1995)) and congenital heart defects (Rosenquist et al., Proc. Natl. Acad. Sci. USA 93, 15227–15232 (1996)) which may be promoted by cobalamin deficiency (Adams et al., Teratology 51, 311–317 (1995)). Cobalamin, and therefore the composition of the invention, may also be generally effective in the prophylaxis of birth defects induced by drugs and teratogens (Mann & Gautieri, Lancet 1, 1451–1452 (1973); Elmazar et al., Fund. Appl. Toxicol. 18, 389–394 (1992)).

In another application, the composition of the invention may be used to treat impairments of the immune system associated with cobalamin deficiency, such as deficiencies in antibody production (van Dommelen et al., Acta Med. Scand. 174, 193–200 (1963); Fata et al., Ann. Intern. Med. 124, 299–304 (1996)), in T-cell counts (Kubota et al., Am. J. Hematol. 24, 221–223 (1987)) and in microbicidal activity of neutrophils (Skacel & Chanarin, Br. J. Haematol. 55, 203–215 (1983)) and macrophages (Chanarin & Stephenson, J. Clin. Pathol. 41, 759–762 (1988)). Cobalamin, and therefore the composition of the invention, may be especially useful in the prevention or treatment of mycobacterial infections, such as tuberculosis or leprosy (Chanarin & Stephenson, op. cit.). The present composition is also applicable to the treatment of retroviral infection and conditions associated with retroviral infections, including HIV infection and AIDS (Baum et al., AIDS 9, 1051–1056 (1995); Weinberg et al., Blood 86 1281–1287 (1995)), where it is expected to be of even greater efficacy than free cobalamin in increasing CD4+T-cell counts and in inhibiting viral infectivity.

In yet another application, the composition of the invention can be used as an antitumor agent (Tsao et al., Pathobiology 58, 292–296 (1990); Tsao & Myashita, Pathobiology 61, 104–108 (1993)). The present composition may also be used to treat various premalignant lesions associated with cobalamin deficiency, either alone (Brinton et al., Br. J. Cancer 59, 810–813 (1989)) or in combination with other methyl donors such as folate (Heimburger et al., JAMA 259, 1525–1530 (1988); Ran et al., Blood 82, Suppl. 1, 532a (1993)).

In a further application, the inventive composition can be used alone or in combination with various antioxidants to treat imbalances of redox homeostasis (Jocelyn, Biochem. J. 77, 363–368 (1960); Mueller & Will, Am. J. Clin. Nutr. 3, 30–44 (1955)) and other abnormalities of antioxidant metabolism (Cox et al., Clin. Sci. 17, 681–692 (1958)) associated with cobalamin deficiency. More generally, the present composition may also be applied to the treatment of any conditions associated with oxidative stress, inasmuch as oxidavive stress can induce a functional cobalamin deficiency by damaging or destroying the corrin ring of vitamin B12. Examples of conditions which can be treated by administration of the present composition alone or in combination with antioxidants include methylmercury toxicity (Sood et al., Cel. Mol. Biol. 39, 213–219 (1993)), heart disease and cataract (Harding et al., Biochem. Soc. Trans. 24, 881–883 (1996)) and retinal degeneration of various kinds, including diabetic retinopathy, macular degeneration and Batten's disease (Agostinho et al., FASEB J. 11, 154–163 (1997)). Since the production of free radicals in skeletal muscle is a factor limiting endurance during prolonged exercise (Reid et al., J. Clin. Invest. 94, 2468–2474

(1994); Leeuwenburgh & Ji, Arch. Biochem. Biophys. 316, 941–949 (1995)), the composition of the invention may also find application as an enhancer of athletic endurance (cf. Singh et al., Med. Sci. Sports Exerc. 25, 328–334 (1993)).

In addition to the aforementioned uses of cobalamin, and therefore of the compositions of the invention, in treating conditions associated with cobalamin deficiency, cobalamin is known to be effective in a number of applications regardless of whether any recognized deficiency exists. In view of the enhanced cellular uptake of the composition of the invention relative to the cellular uptake of free cobalamin, the present composition is expected to be a superior means of treating such conditions as cyanide poisoning (Zerbe & Wagner, Crit. Care Med. 21, 465–467 (1993)) and nitric oxide toxicity (Greenberg et al., J. Pharmacol. Exp. Ther. 273, 257–265 (1995)). Nitric oxide toxicity plays a pathogenic role in sepsis, endotoxemia and systemic inflammatory response syndrome (Greenberg et al., op. cit.), and therefore the composition of the present invention can be used to treat these conditions and to mitigate their attendant hypotension and mortality. The composition of the invention may also be useful as adjunctive therapy when coadministered with inhaled nitric oxide or with nitric oxide donors. Furthermore, excess nitric oxide production has been linked with autoimmune disorders, chronic inflammatory diseases, neurodegenerative diseases and AIDS, and also with migraine and histamine-induced headache (Olesen et al., NeuroReport 4, 1027–1030 (1993); Lassen et al., NeuroReport 6, 1475–1479 (1995)), stroke (Nowicki et al., Eur. J. Pharmacol. 204, 339–340 (1991)), viral pneumonia (Akaike et al., Proc. Natl. Acad. Sci. USA 93, 2448–2453 (1996)), and viral and bacterial neurological diseases such as meningitis (Zheng et al., J. Virol. 67, 5786–5791 (1993); Koedel et al, Ann. Neurol. 37, 313–323 (1995)). Cobalamin, and therefore the composition of the invention, is expected to be of specific benefit in the treatment of all such conditions of excess nitric oxide production.

Since cobalamin combines with superoxide (Bayston et al., J. Am. Chem. Soc. 91, 2775–2779 (1969)) in much the same manner that it does with cyanide or nitric oxide, cobalamin may likewise mitigate conditions of superoxide toxicity. Superoxide is often coreleased with nitric oxide and has been implicated with nitric oxide in the pathogenesis of AIDS and of various autoimmune, chronic inflammatory, ischemic and neurodegenerative diseases. Excess production of superoxide has also been linked with infection by viral, bacterial, parasitic and fungal pathogens (Fuchs et al., Med. Hypotheses 36, 60–64 (1991)), induction of muscle wasting in cachexia (Buck & Chojkier, EMBO J. 15, 1753–1765 (1996)), photodamage to skin (Darr & Fridovich, J. Invest. Dermatol. 102, 671–675 (1994)), and the generation of clastogenic factors (Emerit, Free Radic. Biol. Med. 16, 99–109 (1994)). Clastogenic factors can induce chromosomal aberrations, sister chromatid exchanges, DNA strand breakage, gene mutations and eventual malignancy in a variety of pathogenic situations, including exposure to ionizing radiation, viruses, tumor-promoting chemicals, asbestos, and herbicides such as paraquat, and in such hereditary chromosomal breakage syndromes as ataxia telangiectasia, Bloom's syndrome and Fanconi's anemia (Emerit, op. cit.). The composition of the present invention is directed toward the treatment of all such consequences of superoxide toxicity.

In similar fashion, cobalamin can be used to catalyze the nonenzymatic oxidation of carbon monoxide (Bayston & Winfield, J. Catalysis 9, 217–224 (1967)) and sulfite (Jacobsen et al., J. Allergy Clin. Immunol. 73, 135 (1984)).

Moreover, the neurotoxicity of carbon monoxide poisoning has been recently linked with excess production of both nitric oxide and superoxide (Ischiropoulos et al., J. Clin. Invest. 97, 2260–2267 (1996)). Cobalamin, and therefore the composition of the invention, is thus applicable to the treatment or prophylaxis of all conditions associated with carbon monoxide toxicity, including smoking in adults and pediatric conditions such as fetal growth retardation, sudden infant death syndrome (Hutter & Blair, Med. Hypotheses 46, 1–4 (1996)) and related conditions (Stevenson et al., J. Pediatrics 94, 956–958 (1979)). Cobalamin, and therefore the present composition, is likewise applicable to the treatment or prophylaxis of sulfite toxicity, including such conditions as allergic reactions to sulfites (Anibarro et al., J. Allergy Clin. Immunol. 90, 103–109 (1992)). Moreover, cobalamin has been reported to mediate the dehalogenation of various halogenated pesticides (Schrauzer & Katz, Bioinorg. Chem. 9, 123–143 (1978)), environmental toxins (Assaf-Anid et al., Appl. Env. Microbiol. 58, 1057–1060 (1992)) and solvents (Krone et al., Biochemistry 30, 2713–2719 (1991)), an effect which may account for the protection afforded by cobalamin in cases of carbon tetrachloride-induced hepatic injury (Kasbekar et al., Biochem. J. 72, 384–389 (1959)). The composition of the present invention is thus directed also toward the treatment or prophylaxis of toxicity caused by exposure to halogenated hydrocarbons and to the enhancement of environmental bioremediation of halogenated hydrocarbons by anaerobic bacteria (Hashsham et al., Environ. Sci. Technol. 29, 2856–2863 (1995)).

In additional applications independent of the presence of cobalamin deficiency, the composition of the invention can be administered to treat cases of asthma (Crocket, Acta Allergol. 11, 261–268 (1957)) and dermatitis (Simon, J. Allergy 22, 183–185 (1951)). Moreover, the known properties of cobalamin as an antagonist of histamine (Ata, in *Vitamin B12und Intrinsic Factor* (Stuttgart: Ferdinand Enke Verlag, 1957), 543–553) suggest the use of the present composition as an antihistamine in the treatment of allergy, anaphylactic shock and other conditions. In particular, the activity of cobalamin in mitigating the toxic effects of histamine suggests a novel application of cobalamin, and therefore of the composition of the invention, in the treatment of vascular headache induced by consumption of wine, cheese and other histamine-containing food and drink (Jarisch & Wantke, Int. Arch. Allergy Immunol. 110, 7–12 (1996)). Furthermore, the composition of the invention can also be applied to the treatment of oversedation due to intoxication with sedatives and/or alcohol (Newbold, Med. Hypotheses 30, 1–3 (1989)). In view of the efficacy of cobalamin, and therefore of the present composition, in treating intoxication with alcohol, in promoting mental acuity in general, and in treating allergic reactions due to histamine and sulfites in wine and other alcoholic beverages, the present composition may be especially useful in ameliorating a broad range of toxic reactions associated with alcohol consumption.

The present composition can also be used to accelerate recovery from anorexia nervosa by enhancing weight gain, normalizing gastrointestinal function, alleviating latent fatigue and increasing mental performance (Korkina et al., Zhur. Nevropat. Psikhiat. 89, 82–87 (1989)). In related applications the composition can be administered to relieve fatigue and promote well-being even in nominally healthy individuals (Ellis & Nasser, Br. J. Nutr. 30, 279–283 (1973)), and to improve cognitive ability and physical stamina by enhancing the biosynthesis of choline and acetylcholine (Sasaki et al., Pharmacol. Biochem. Behav. 43, 635–639 (1992)). The present composition can also be administered to normalize the entrainment of circadian rhythms in persons suffering from sleep disorders, possibly by increasing the sensitivity of the circadian clock (Honma et al., Experientia 48, 716–720 (1992)). Likewise, the composition can be administered to adjust the circadian rhythms of individuals suffering from "jet lag."

Additional applications of the composition of the invention include treatment of viral conditions and potentiation of immunostimulation by interferon. Cobalamin has been shown to be useful in promoting recovery from viral conditions such as hepatitis (Kelemen et al., Int. Z. Vitaminforsch. 31, 307–316 (1961)), poliomyelitis (Leroy & Robin, Semaine hop. Paris 31, 1097–1098 (1955)), and herpetic eruptions such as those due to shingles (MacLatchy, Br. J. Ophthal. 40, 762–764 (1956); King, N.Z. Med. J. 105, 135 (1992)). In view of the reported efficacy of cobalamin in treating both shingles (i.e., the postinfectious reemergence of herpes zoster) and also poliomyelitis, cobalamin and therefore the composition of the invention are expected to be useful in the treatment of postpolio syndrome. In treating viral infections the composition of the invention can be used either alone or in combination with substances such as interferons. Various interferons have been used in the treatment of viral infections such as those due to herpes zoster and HIV, and in the treatment of cancer and multiple sclerosis as well. Recently it has been shown that cobalamin can potentiate the immunomodulation induced by interferon (Medenica et al., Blood 86, Suppl. 1, 850a (1995)). In the latter study vitamin B12 was coadministered with interferon to patients suffering from prostate cancer, colon cancer or herpes zoster. As compared to controls receiving only interferon, treatment with cobalamin (and by inference with the composition of the invention) can increase serum interferon levels, decrease levels of natural interferon inhibitory factor, enhance immunocyte activity and reduce muscle pain which arises as a side effect of interferon treatment.

With regard to its activity in relieving pain, vitamin B12 has long been recognized as an effective analgesic either alone (Surtees & Hughes, Lancet 1, 439–441 (1954)) or in combination with other B vitamins (Leuschner, Arzneim.-Forsch./Drug Res. 42, 114–115 (1992)). Moreover, adenosylcobalamin has been recently shown to potentiate the antinociceptive effects of various opioids such as morphine and enkephalin (Villanueva et al., J. Pharmacol. Exp. Ther. 257, 1198–1202 (1991)). Also, treatment of osteoarthritis with both cobalamin and folate has been reported to result in fewer tender hand joints, as compared to treatment with prescribed nonsteroidal anti-inflammatory drugs (Flynn et al., J. Am. Coll. Nutr. 13, 351–356 (1994)); the beneficial effects of cobalamin and folate therapy in osteoarthritis may be mediated in part by enhanced production of S-adenosylmethionine (diPadova, Am. J. Med. 83, Suppl. 5A, 60–65 (1987)) as well as by the antinociceptive effects of cobalamin. These results suggest the use of the composition of the invention as an analgesic in general and as a treatment for osteoarthritis, either alone or in combination with other vitamins or medications.

In another application independent of the presence of cobalamnin deficiency, the composition of the invention can be used to promote epithelial cell growth and the healing of aphthous ulcers and other lesions in mucosal tissues (Ansell, Lancet 2, 994 (1962)). The present composition can also be applied to enhance recovery of cardiac muscle in myocardial infarction (Nikolaeva et al., Circ. Res. 35, Suppl. III, 202–213 (1974)), and to promote wound healing in general (Findlay, Proc. Soc. Exp. Biol. Med. 82, 492–495 (1953)). In view of the enhancement of insulin sensitivity promoted by cobalamin administration and the fact that insulin can be used to treat severe burns (Davies, New Scientist Dec. 2, 1995, p. 20), the present composition may be useful for potentiating the anabolic effects of insulin during recovery from burns and other traumatic injury. The enhanced cellular uptake demonstrated by the composition of the invention renders it especially useful when applied topically, alone or with accompanying oral administration, to promote the healing of skin conditions including burns, sunburn, wounds, ulcers, lacerations, herpetic eruptions, psoriasis, dermatoses and eczema, among other conditions. A further application for the composition of the invention is in the detoxification of poisoning caused by such heavy metals as cadmium (Couce et al., J. Inorg. Biochem. 41, 1–6 (1991)), lead (Kleinsorge et al., Zschr. inn. Med. 9, 903–906 (1954)) and mercury (e.g., methylmercury, Sood et al., Cell. Mol. Biol. 39, 213–219 (1993)) and such non-metals as selenium (Chen & Whanger, Toxicol. Appl. Pharmacol. 118, 65–72 (1993)). Finally, cobalamin and therefore the composition of the invention may be generally useful in the treatment of convulsions caused by various agents and medications (Ata, in *Vitamin B12 und Intrinsic Factor* (Stuttgart: Ferdinand Enke Verlag, 1957), 544–553) and in the treatment of febrile convulsions (Osifo et al., J. Neurol. Sci. 68, 185–190 (1985)).

A further application of the present composition is as a component of a diagnostic assay for determining cobalamin deficiency, even in the absence of hematological abnormalities or in the presence of high serum cobalamnin levels. This application is based on the finding that the extent of uptake of cobalamin in the form of a composition of the invention relative to the extent of uptake of free cobalamin appears to be directly correlated with the severity of the cobalamin deficiency and/or defect in cobalamin binding and transport. To assay for cobalamin deficiency, a blood sample is withdrawn from an individual and placed in contact with the composition. The extent of cellular uptake of cobalamin from the composition relative to cellular uptake of free cobalamin is then determined. Specifically, a blood sample is obtained and divided into two fractions. Cobalamin in the form of a composition of the invention and free cobalamin are each added to separate fractions. Following a period of time sufficient to allow cellular uptake of cobalamin, the samples are centrifuged. Red blood cells (RBC) are then extracted from the sample and lysed. The amount of cobalamin taken up by RBC in each of the samples is then determined, such as by radioisotope dilution assay or microbiological assay, for example. The extent of enhanced uptake of cobalamin in the form of the composition of the invention relative to cobalamin alone indicates the severity of the deficiency or defect. Alternatively, a similar procedure can be carried out using cells other than RBC extracted from an individual, such as bone marrow aspirates obtained from biopsy or mucosal cells obtained from buccal scraping, for example. Such a procedure may be usefuil for determining the presence of a cobalamin deficiency localized to specific cells or tissues. For general purposes, however, the form of the assay utilizing RBC is preferred.

Administration of a composition of the present invention to an individual can be carried out using known procedures at dosages and for periods of time effective to result in the desired therapeutic response, such as an increase in depressed serum or tissue cobalamin levels and/or clinical remission of symptoms. An active amount of the composition in a physiologically acceptable carrier can be administered orally as a solid or liquid, sublingually, intranasally, topically or by injection. The compositions of the invention can be administered in slow release forms, such as by depot injection (e.g., in a carrier which slows the absorption of the inventive composition) or by compounding in a sustained release tablet. Effective amounts of the composition of the invention will vary according to factors such as the age, sex and weight of the individual. Dosage regimens may be adjusted to provide the optimum therapeutic response. For example, for the treatment of cobalamin deficiency in an individual the loading dose of cobalamin typically ranges from 1000 µg per day to 1000 µg per week, administered intramuscularly. Because crystalline cobalamin may be inefficiently absorbed orally, especially in the absence of intrinsic factor, the optimal therapeutic dose recommended for oral administration is usually at least 1000 µg per day. Given the increased uptake of the composition relative to free cobalamin, smaller dosages and/or alternative means of administration may be available. For example, the composition may be administered orally or sublingually at a dosage of 100 µg of cobalamin per day. A therapeutic response may be achieved with dosage as small as 5 to 50 µg of cobalamin daily, administered orally or sublingually.

The composition of the invention may be combined with other factors to provide increased therapeutic effectiveness. Such factors may include vitamins, minerals, antioxidants and/or other biomolecules, drugs, medicinals, herbal preparations and microorganisms, wherever compatible with the composition of the invention. For example, the composition of the invention may be combined or coadministered with folates to treat osteoarthritis (Flynn et al., J. Am. Coll. Nutr. 13, 351–356 (1994)), prevent neural tube defects (Mills et al., Lancet 345, 149–151 (1995)), treat premalignant lesions (Ran et al., Blood 82, Suppl. 1, 532a (1993); Heimburger et al., JAMA 259, 1525–1530 (1988)), or prevent exacerbation of cobalamin-deficient neuropathology induced by folate supplementation (Carmel & Johnson, Blood 86, Suppl. 1, 644a (1995)). The composition of the invention may also be combined or coadministered with other B vitamins to treat diabetic neuropathy (Sakitama et al., J. Nutr. Sci. Vitaminol. 35, 95–99 (1989)) or provide pain relief (Leuschner, Arzneim.-Forsch./Drug Res. 42, 114–115 (1992)), and with other vitamins and nutrients to treat atherosclerotic conditions (Olszewski et al., Atherosclerosis 75, 1–6 (1989); Olszewski, ibid. 88, 97–98 (1991)), vitiligo (Montes et al., Cutis 50, 39–42 (1992)) and Down's syndrome (Harrell et al., Proc. Natl. Acad. Sci. USA 78, 574–578 (1981)). In other examples, the composition of the invention may be combined or coadministered with interferon to enhance imnunomodulation (Medenica et al., Blood 86, Suppl. 1, 850a (1995)), with opioids such as morphine and enkephalins to potentiate antinociception (Villanueva et al., J. Pharmacol. Exp. Ther. 257, 1198–1202 (1991)), and with folates and fluoropyrimidines to potentiate antitumor effects (Tisman et al., Clin. Res. 33, 459A (1985)). The present composition may also be combined with microorganisms such as Bifidobacteria to promote immunoenhancement (De Simone et al., Int. J. Immunother. 9, 23–28 (1993)) and inhibit carcinogenesis (Pierra et al., Cancer Res 57, 225–228 (1997)), among other effects. The composition of the invention and additional factors may be administered together as a single composition or simultaneously or sequentially in two or more separate compositions.

To administer a composition of the invention by other than parenteral administration, it may be necessary to coat the composition or coadminister the composition with a material to prevent its inactivation. For example, the composition may be administered to an individual in an appropriate diluent or in an appropriate carrier such as liposomes. Pharmaceutically acceptable diluents include solutions of glycerol, polyalcohols, saline and aqueous buffer solutions. Without wishing to be bound by theory, the inventors believe that in certain embodiments saline solution can decrease the efficacy of the compositions of the invention. Thus, the diluent is preferably selected to ensure maximal activity for the inventive complex. In certain preferred embodiments, the diluent is not a saline solution, e.g., does not comprise significant amounts of salt. Liposomes include water-in-oil-in-water CGF emulsions as well as conventional liposomes (Strejan et al., J. Neuroimmunol. 7, 27–41 (1984)).

Dispersions for parenteral or intraperitoneal administration can be prepared in glycerol, liquid polyethylene glycols and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In general, the inventive compositions are appreciably soluble in water, and sterile aqueous solutions are preferred. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or medium containing, for example, water, ethanol, polyols (such as glycerol, propylene glycol, liquid polyethylene glycol and the like), suitable mixtures thereof and vegetable oils. It is believed that in certain embodiments, ethanol can degrade the efficacy of the inventive compositions. Thus, in some preferred embodiments, the carrier medium does not comprise significant amounts of ethanol. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents. In many cases, it will be preferable to include isotonic agents, e.g., sugars and polyalcohols such as mannitol and sorbitol, in the composition. Prolonged absorption of the injectable compositions can be brought about by including in the composition an agent which delays absorption, for example, aluminum monostearate or gelatin.

For further examples of pharmaceutical formulations suitable for administration of the compositions of the invention, see, e.g., *Remington's Pharmaceutical Sciences,* 17th ed. (Easton, Pa.: Mack Publishing Company, 1985).

Sterile injectable solutions can be prepared by incorporating the composition in an appropriate solvent with one or a combination of ingredients enumerated above, as required. Generally, dispersions are prepared by incorporating the composition into a sterile vehicle which contains a dispersion medium and the required other ingredients from those enumerated above.

The composition may be orally administered, for example, with an inert diluent or an assimilable edible carrier. The composition and other ingredients may also be enclosed in a hard or soft shell gelatin capsule, compressed into tablets, or incorporated directly into the individual's diet. For oral therapeutic administration, the composition may be incorporated with excipients and used in the form of ingestible tablets, buccal tablets, troches, capsules, elixirs, suspensions, syrups, wafers and the like. The amount of active compound (i.e., cobalamin) in such therapeutically useful compositions is such that a suitable dosage will be obtained.

The tablets, troches, pills, capsules and the like may also contain a binder, an excipient, a lubricant or a sweetening agent. Various other materials may be present as coatings or to otherwise modify the physical form of the dosage unit. For instance, tablets, pills or capsules may be coated with shellac, sugar or both. Of course, any material used in preparing any dosage unit form should be pharmaceutically pure and substantially nontoxic in the amounts employed.

As used herein, "pharmaceutically acceptable carrier" includes any appropriate solvents, dispersion media, coatings, antibacterial and antifingal agents, isotonic and absorption delaying agents and the like. The use of such media and agents for pharmaceutically active substances is well known in the art. Except insofar as any conventional medium or agent is incompatible with the active compound, use thereof in compositions of the invention is contemplated.

It is especially advantageous to formulate compositions of the invention in dosage unit form for ease of administration and uniformity of dosage. Dosage unit form as used herein refers to physically discrete units suited as unitary dosages for the individuals to be treated. Each dosage contains a predetermined quantity of active compound (i.e., cobalamin) calculated to produce the desired therapeutic effect in association with the required pharmaceutical carrier. The specification for the novel dosage unit forms of the invention is dependent on the unique characteristics of the composition and the particular therapeutic effect to be achieved. Dosages are determined by reference to the usual dose and manner of administration of the ingredients.

The invention is further illustrated by the following, non-limiting examples. The contents of all references cited in this application are hereby incorporated by reference.

EXAMPLE 1

Preparation of Compositions of Cobalamin

A composition of the invention in a molar ratio of about 1:2:4 was prepared by dissolving 5 grams of crystalline cyanocobalamin, 1.08 grams of L-lysine and 2.16 grams of L-glutamine (all from Sigma Chemical Co., St. Louis, Mo.) at room temperature in 1 liter of distilled water. The resulting stock solution was stored under sterile conditions for a period of three weeks. Aliquots of the resulting composition (CN-Cbx) were then withdrawn in sterile fashion. Some aliquots were mixed with folates, minerals or both; others were further diluted with distilled water or with solutions of glycerol to yield compositions containing 1 mg cyanocobalamin per ml., or crystallized to yield the composition in dried form. Additional compositions in the molar ratio 1:2:4 were prepared utilizing hydroxocobalamin instead of cyanocobalamin.

EXAMPLE 2

Analysis of Cellular Uptake of Cobalamin

Blood was drawn from three subjects, one presumptively normal (N), one with recurrent gastritis of moderate severity (G) and one with a chronic intracellular vitamin B12 deficiency refractory to conventional therapy (D). Blood samples were divided in half and each half incubated separately at 37° C. with aliquots of cyanocobalamin (CN-Cbl) or cobalamin in the form of a composition with lysine and glutamine in a molar ratio of about 1:2:4 as described above (CN-Cbx). Each solution was calculated to contain 200 μg of cyanocobalamin. Aliquots of equal size of each solution were also added to saline blanks. After two hours red blood cells (RBC) were separated by centrifugation and washed in phosphate-buffered saline. Contents of the RBC were then extracted in warm ethanol, and cobalamin levels of each sample and of each blank were determined by radioisotope dilution assay (RIDA).

The relative uptake of cobalamin for each sample was determined by dividing the measured cobalamin content of the sample by the measured cobalamin content of the respective blank. The ratios of relative uptake for samples incubated with CN-Cbl versus CN-Cbx for each individual were calculated, and the results expressed in percentage form. In all three cases this percentage was positive, indicating that RBC take up cobalamin in the form of the present invention preferentially over free cobalamin. The actual results for the three subjects are as follows: N, 5% enhanced uptake; G, 16% enhanced uptake; and D, 62% enhanced uptake. Thus, the extent of the enhancement of cobalamin uptake from the composition may be directly correlated with the severity of known vitamin B12 deficiency and/or defect in vitamin B12 binding or transport.

EXAMPLE 3

Blood was drawn from two subjects, one with untreated attention deficit disorder (A) and one with a progressive cardiovascular disease undetected at that time (C). Blood samples were centrifuged, plasma and buffy coat discarded, and the RBC washed and resuspended in phosphate-buffered saline at equalized hematocrit. Suspensions of RBC were divided in half and each half incubated separately at 37° C. with aliquots of CN-Cbl or CN-Cbx as described previously. Each solution was calculated to contain 100 ng of cyanocobalamin. Aliquots of equal size of each solution were also added to saline blanks. After 1½ hours RBC were centrifuged and the supernatant separated. Cobalamin levels of the supernatant of each sample and of each saline blank were determined by microbiological assay (Vitamin Diagnostics, Lawrence Harbor, N.J.).

The uptake of cobalamin by RBC for each sample was inferred by subtracting the measured cobalamin content of each supernatant from the measured cobalamin content of the appropriate blank. The relative uptake of cobalamin by RBC was then determined by dividing the inferred RBC uptake by the cobalamin content of the respective blank. The ratios of relative uptake for samples incubated with CN-Cbl versus CN-Cbx were calculated for each subject and the results expressed in percentage form. Both subjects demonstrated preferential uptake by RBC of cobalamin, in agreement with previous results. The calculated results were: A, 22% enhanced uptake and C, 87% enhanced uptake. Thus , the extent of enhancement of cobalamin uptake from the composition of the invention may be directly correlated with the severity of the presumed B12-deficiency and/or B12-deficient disease state.

EXAMPLE 4

A composition of the invention can be prepared by adding 5 milligrams of crystalline cyanocobalamin, 1.08 milligrams of L-lysine and 2.16 milligrams of L-glutamine at room temperature or above to one quart whole milk (preferably milk which has been scalded and then cooled prior to addition of the above components). Yoghurt culture starter containing dried streptococcus thermophilus, *Lactobacillus bulgaricus* and *Lactobacillus acidophilus* (available from VMC Corp., Montreal, Quebec) is then added, and the milk is stirred to provide a uniform niixture, which is then incubated at room temperature or above (preferably between about 37° and 45° C.) for 4–12 hours (e.g., preferably about 4 hours at 45° C.) to provide yoghurt enriched in a composition of the invention. A yoghurt so constituted for consumption will provide about 470 micrograms of cobalamin per 3 ounce serving.

Another yoghurt-based composition can be made by adding 250 milligrams of crystalline cyanocobalamin, 67 milligrams of L-lysine monohydrochloride and 108 milligrams of L-glutamine to one quart skim milk. The milk is cultured with lactobacilli as above, and the resulting yoghurt is dried (e.g., by freeze-drying or spray drying) to provide about 375 micrograms of cobalamin per 200 mg of the dried product. The dried product can be packaged, e.g., in gelatin capsules, or added to other foods. Alternatively, after the yogurt has been cultured and allowed to separate, the resulting yoghurt whey can be collected and concentrated or dried. Yoghurt whey so enriched in a composition of the invention may be consumed directly or incorporated into products such as frozen yoghurt.

EXAMPLE 5

A unit dose of a composition of the invention can be formulated as follows: about 500 million each *L. acidophilus* and *L. bifidus*, 400 μg of cyanocobalamin, 200 mg of glutamine, 62.5 mg lysine monohydrochloride, and 50 mg fructooligosaccharides are combined in dry form and encapsulated together in a standard #0 gelatin capsule. Each capsule thus provides about 400 micrograms of cobalamin per dose.

The contents of all references cited herein are hereby incorporated by reference.

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A composition comprising a mixture in a pharmaceutically acceptable carrier of:
   (a) cobalamin;
   (b) a first isolated amino acid selected from the group consisting of lysine and arginine; and
   (c) a second isolated amino acid selected from the group consisting of glutamine, tyrosine, serine, threonine, and asparagine, in a molar ratio of from about 1:0.1:0.1 to about 1:100:100, wherein (a), (b), and (c) are dissolved in sterile water, and wherein the amounts of (b) and (c) act in concert enhance the cellular uptake of (a) in vivo when compared to the uptake of (a) alone or the uptake of (a) in combination with casein, or (b) alone, or (c) alone.

2. The composition of claim 1 comprising cobalamin, lysine and glutamine in a molar ratio of about 1:2:4.

3. The composition of claim 1 comprising cobalamin, lysine, glutamine and tyrosine in a molar ratio of about 1:2:2:2.

4. The composition of claim 1, wherein the composition further comprises a microorganism capable of catalyzing the formation of a cobalamin:amino acid complex.

5. A method of increasing cellular uptake of cobalamin in the cells of a subject, comprising administering to the subject an active amount of a composition comprising a mixture of:
   (a) cobalamin;
   (b) a first isolated amino acid selected from the group consisting of lysine and arginine; and
   (c) a second isolated amino acid selected from the group consisting of glutamine, tyrosine, serine, threonine, and asparagine, wherein (a), (b), and (c) are dissolved in sterile water, and wherein the amounts of (a), (b), and (c) are combined in a molar ratio of from about 1:.1:0.1, respectively, to about 1:100:100, respectively, such that the amounts of (a), (b), and (c) act in concert to increase the cellular uptake of cobalamin in the cells of the subject when compared to the uptake of cobalamin alone or the uptake of cobalamin in combination with casein, or (b) alone, or (c) alone.

6. The method of claim 5, wherein the composition comprises a pharmaceutically acceptable carrier.

7. A method for treating a condition associated with cobalamin deficiency in a subject, the method comprising:
   administering to a subject in need thereof a therapeutically effective amount of a composition of claim 1, such that a condition associated with cobalamin deficiency in the subject is treated.

8. The method of claim 7, wherein the subject is a human.

9. The method of claim 8, wherein the condition is Alzheimer's disease.

10. The method of claim 7, wherein the condition is a condition associated with retroviral infection.

11. The method of claim 10, wherein the condition is HIV infection.

12. The method of claim 7, wherein the cellular uptake of cobalamin in the cells of the subject is increased without the use of carrier proteins.

13. The method of claim 12, wherein the subject is a human.

14. The method of claim 12, wherin the condition is characterized by low levels of cobalamin in the nervous system.

15. The method of claim 14, wherein the condition is characterized by low levels of cobalamin in cerebrospinal fluid.

16. The method of claim 14, wherein the condition is peripheral neuropathy.

17. The method of claim 16, wherein the condition is diabetic neuropathy.

* * * * *